(12) United States Patent
Lim et al.

(10) Patent No.: US 8,425,561 B2
(45) Date of Patent: Apr. 23, 2013

(54) INTERSPINOUS PROCESS BRACE

(75) Inventors: Roy K. Lim, Germantown, TN (US); Thomas A. Carls, Memphis, TN (US); Aurelien Bruneau, Jacksonville, FL (US); Eric C. Lange, Pleasanton, CA (US); Kent M. Anderson, San Jose, CA (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/114,191

(22) Filed: May 24, 2011

(65) Prior Publication Data
US 2011/0238114 A1    Sep. 29, 2011

Related U.S. Application Data

(62) Division of application No. 11/413,616, filed on Apr. 28, 2006, now abandoned.

(51) Int. Cl.
*A61B 17/70* (2006.01)
(52) U.S. Cl.
USPC ............................ 606/249; 606/248; 606/283

(58) Field of Classification Search .......... 606/248–249, 606/283, 70, 71
See application file for complete search history.

(56) References Cited

U.S. PATENT DOCUMENTS

| | | | | |
|---|---|---|---|---|
| 5,972,022 | A * | 10/1999 | Huxel | 606/215 |
| 6,626,944 | B1 * | 9/2003 | Taylor | 623/17.16 |
| 2005/0010225 | A1 * | 1/2005 | Del Medico | 606/69 |
| 2005/0085814 | A1 * | 4/2005 | Sherman et al. | 606/61 |
| 2005/0261768 | A1 * | 11/2005 | Trieu | 623/17.11 |
| 2006/0235387 | A1 * | 10/2006 | Peterman | 606/61 |

* cited by examiner

*Primary Examiner* — Eduardo C Robert
*Assistant Examiner* — Julianna N Harvey
(74) *Attorney, Agent, or Firm* — Sorell Lenna & Schmidt LLP

(57) ABSTRACT

An interspinous process brace is disclosed and can include a superior component and an inferior component. The superior component can include a superior spinous process bracket that can engage a superior spinous process. The inferior component can include an inferior spinous process bracket that can engage an inferior spinous process. Further, the interspinous process brace can be moved between a bent configuration and a straight configuration. In the bent configuration, an overall height of the interspinous process brace can be minimized to facilitate installation between the superior spinous process and the inferior spinous process.

14 Claims, 21 Drawing Sheets

INTERSPINOUS PROCESS BRACE

FIELD OF THE DISCLOSURE

The present disclosure relates generally to orthopedics and orthopedic surgery. More specifically, the present disclosure relates to devices used to support adjacent spinous processes.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

BRIEF DESCRIPTION OF THE DRAWINGS

FIG. 16 is a side plan view of the third interspinous process spacer in a straight configuration with a posterior locking plate and an anterior locking plate disengaged there from.

DETAILED DESCRIPTION OF THE DRAWINGS

Figure 1:
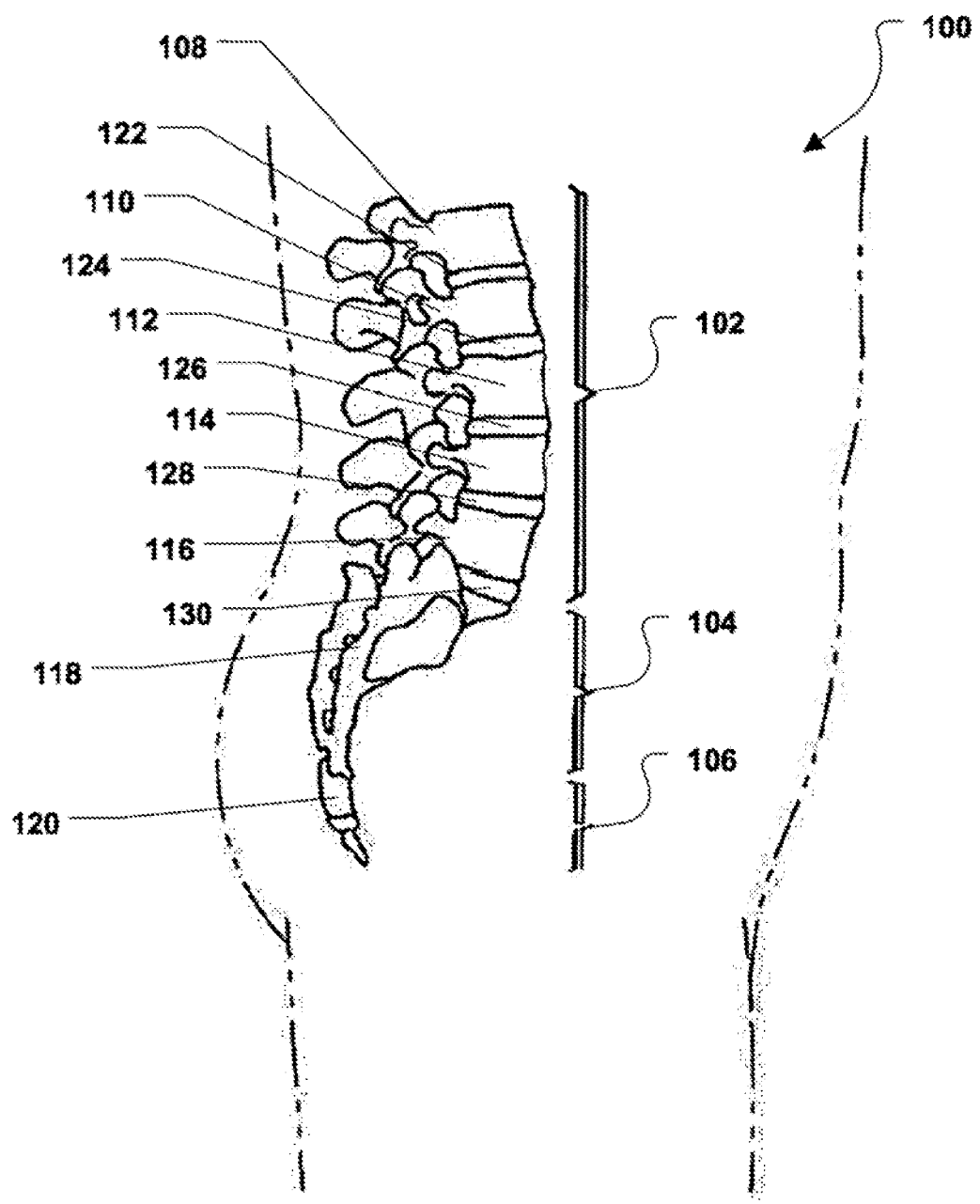
FIG. 1 is a lateral view of a portion of a vertebral column.

An interspinous process brace is disclosed and can include a superior component and an inferior component. The superior component can include a superior spinous process bracket that can engage a superior spinous process. The inferior component can include an inferior spinous process bracket that can engage an inferior spinous process. Further, the interspinous process brace can be moved between a bent configuration and a straight configuration. In the bent configuration, an overall height of the interspinous process brace can be minimized to facilitate installation between the superior spinous process and the inferior spinous process.

In another embodiment, an interspinous process brace is disclosed and can include a superior spinous process bracket and an inferior spinous process bracket. The superior spinous process bracket can engage a superior spinous process and the inferior spinous process bracket can engage an inferior spinous process. The interspinous process brace can also include a central component that can connect the superior spinous process bracket and the inferior spinous process bracket. Additionally, the central component can be configured to allow the interspinous process brace to move between a bent configuration and a straight configuration. In the bent configuration an overall height of the interspinous process brace can be minimized to facilitate installation between the superior spinous process and the inferior spinous process.

In still another embodiment, a method of treating a spine is disclosed and can include moving an interspinous process brace to a bent configuration and installing the interspinous process brace between a superior spinous process and an inferior spinous process. Further, the method can include returning the interspinous process brace to a straight configuration between the superior spinous process and the inferior spinous process.

In yet another embodiment, a method of treating a spine is disclosed and can include distracting a superior spinous process and an inferior spinous process, moving an interspinous process brace to a bent configuration, and installing the interspinous process brace between the superior spinous process and the inferior spinous process. Also, the method can include returning the interspinous process brace to a straight configuration between the superior spinous process and the inferior spinous process.

In still yet another embodiment, a kit is disclosed and can include at least two interspinous process braces. Each interspinous process brace can include a superior component and an inferior component. The superior component of each interspinous process brace can include a superior spinous process bracket that can engage a superior spinous process. Also, the inferior component of each interspinous process brace can include an inferior spinous process bracket that can engage an inferior spinous process. Moreover, the interspinous process brace can be moved between a bent configuration and a straight configuration. In the bent configuration, an overall height of the interspinous process brace can be minimized to facilitate installation between the superior spinous process and the inferior spinous process.

In another embodiment, a kit is disclosed and can include an interspinous process brace. The interspinous process brace can include a superior component and an inferior component. The superior component can include a superior spinous process bracket that can engage a superior spinous process. The inferior component can include an inferior spinous process bracket that can engage an inferior spinous process. Further, the interspinous process brace is movable between a bent configuration and a straight configuration. In the bent configuration, an overall height of the interspinous process brace can be minimized to facilitate installation between the superior spinous process and the inferior spinous process. The kit can also include a locking pin that can be configured to engage the interspinous process brace.

In still another embodiment, a method of treating a spine is disclosed and can include moving an interspinous process brace to a bent configuration and installing the interspinous process brace between a superior spinous process and an inferior spinous process. Further, the method can include returning the interspinous process brace to a straight configuration in order to distract the superior spinous process and the inferior spinous process.

Description of Relevant Anatomy

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, treatment of that intervertebral lumbar disc 122, 124, 126, 128, 130 can be effected in accordance with one or more of the embodiments described herein.

Figure 2:
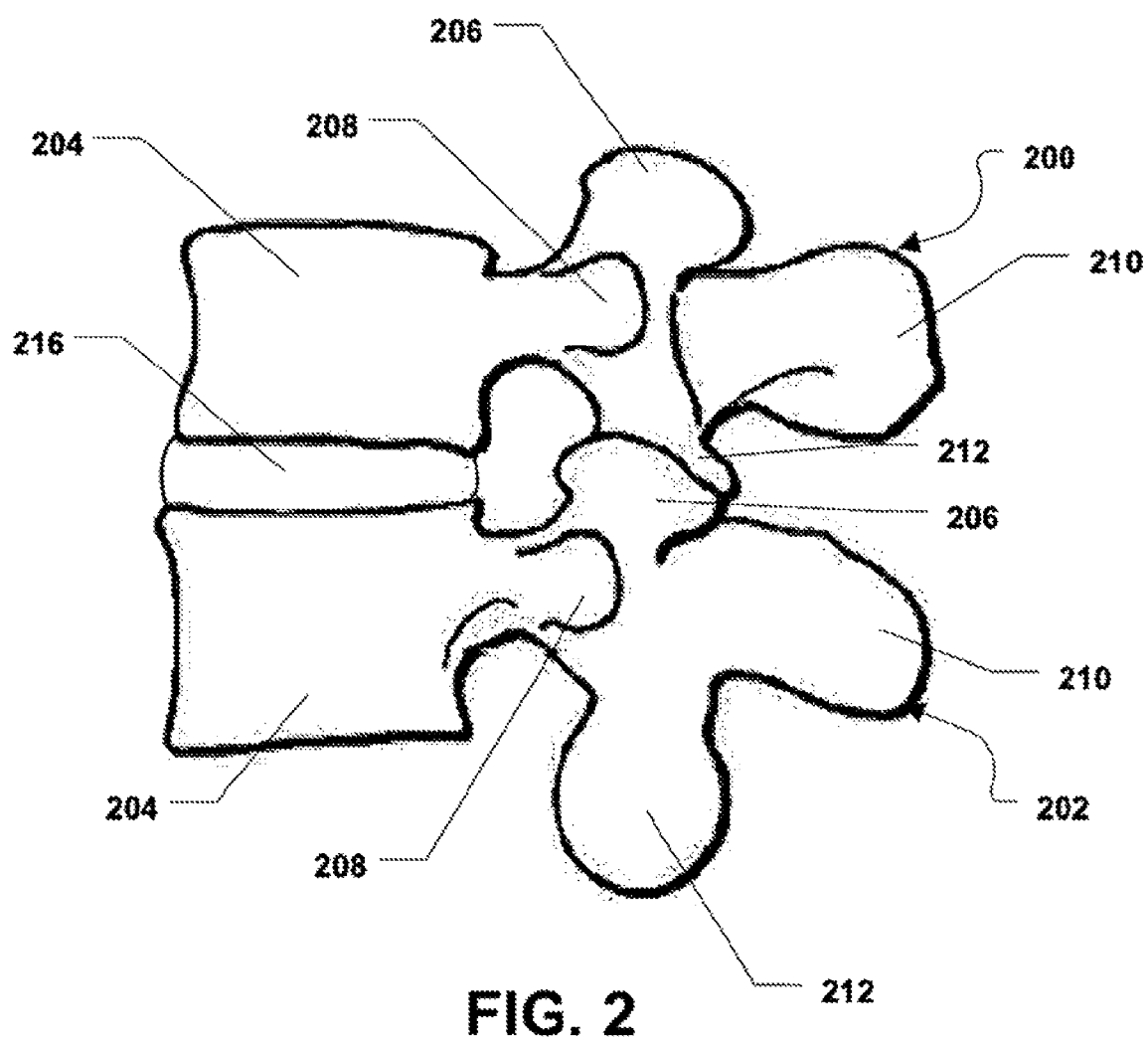
FIG. 2 is a lateral view of a pair of adjacent vertrebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
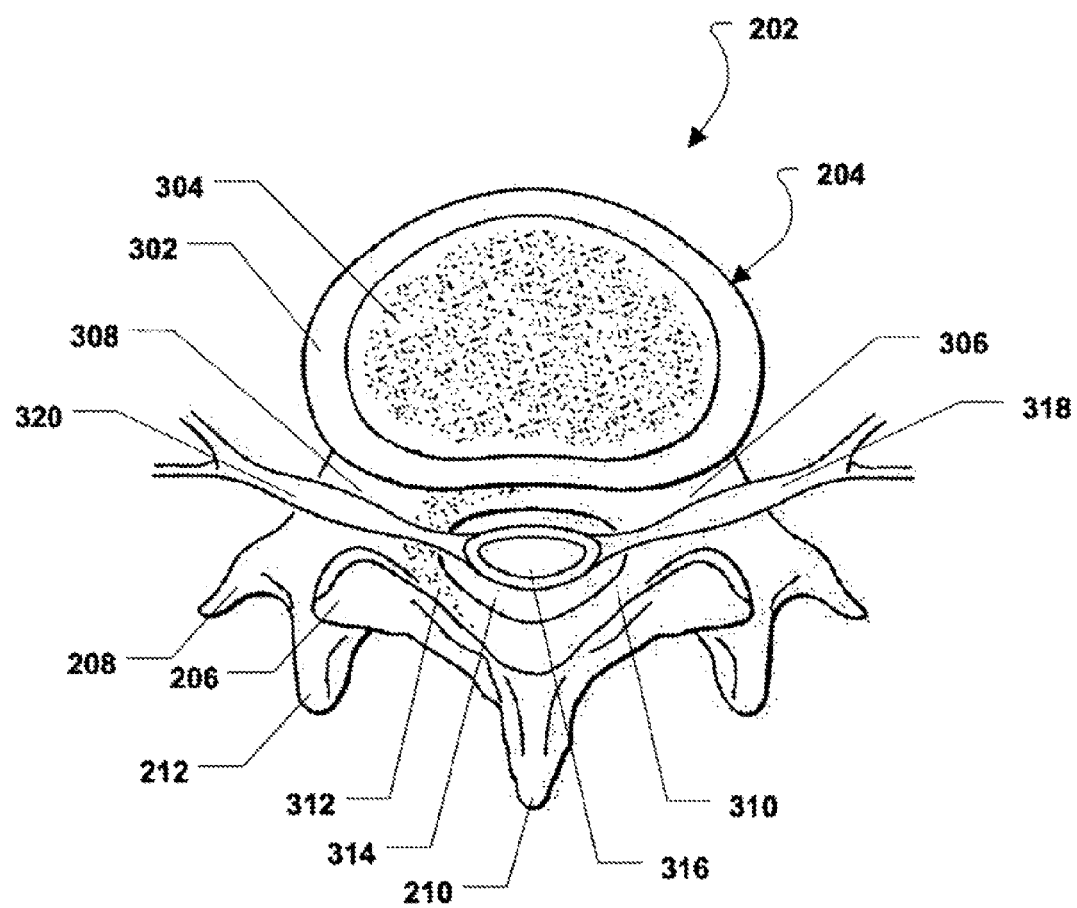
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a First Embodiment of an Interspinous Process Brace

Figure 4:
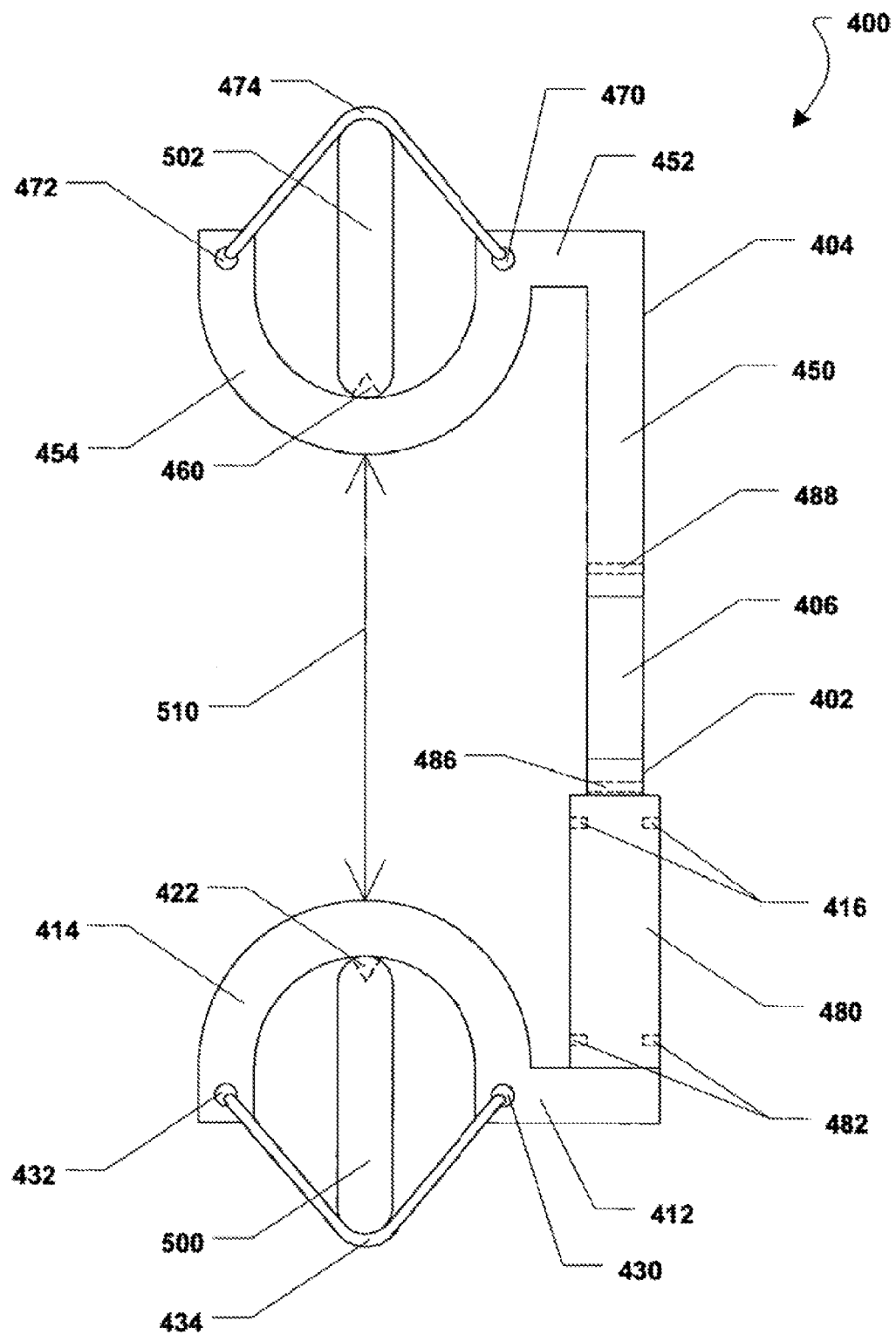
FIG. 4 is a rear plan view of a first interspinous process spacer with a locking sleeve unlocked.
Figure 5:
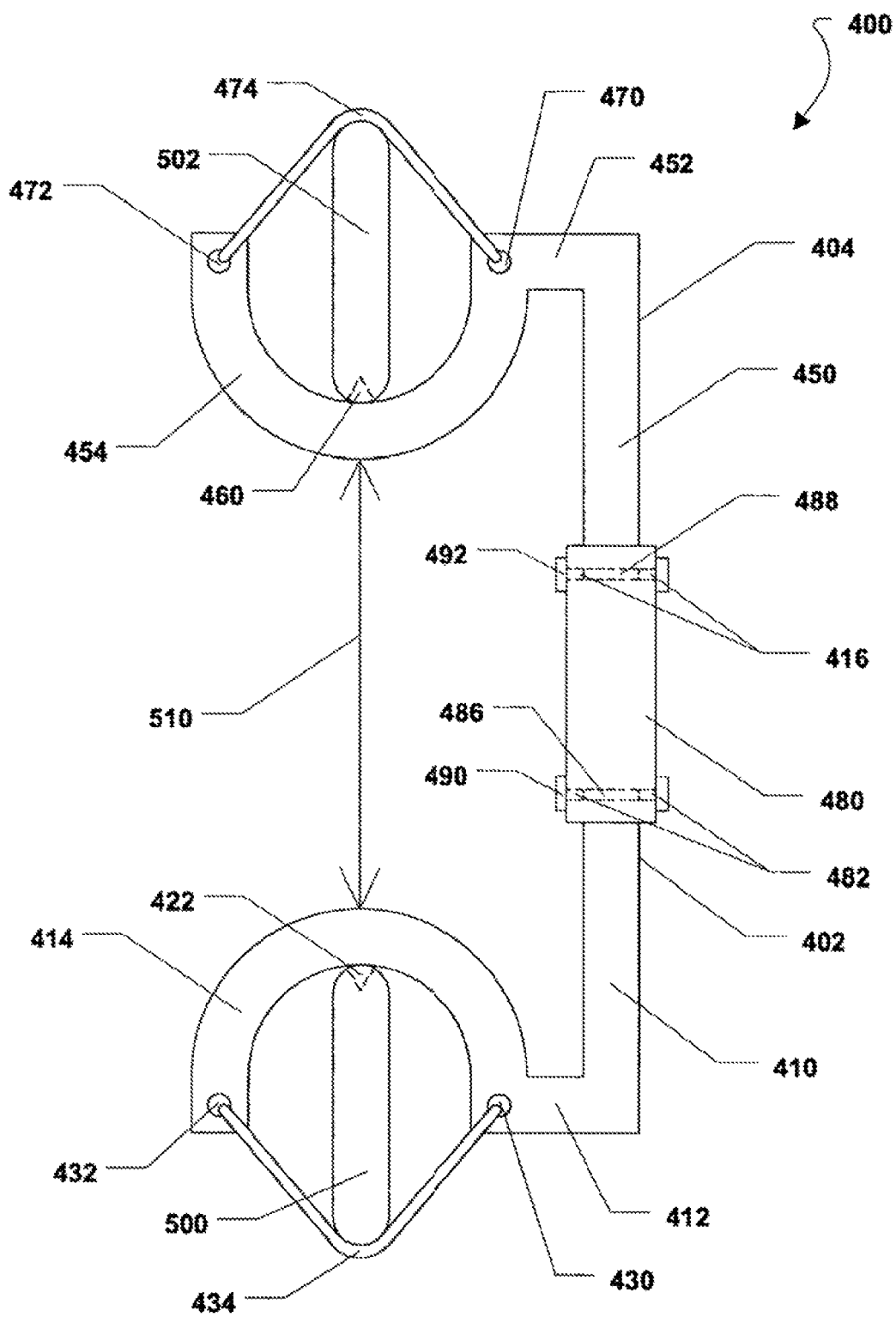
FIG. 5 is a rear plan view of the first interspinous process spacer with the locking sleeve locked.

Referring to FIG. 4 through FIG. 8, a first interspinous process brace is shown and is generally designated 400. As shown in FIG. 4 and FIG. 5, the interspinous process brace 400 can include an inferior component 402 and a superior component 404. Further, the inferior component 402 can be coupled, or otherwise connected, to the superior component 404 via a central component 406. In a particular embodiment, the components 402, 404, 406 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the components 402, 404, 406 can be made from any other substantially rigid biocompatible materials.

In a particular embodiment, the components 402, 404, 406 can be made from the same biocompatible material. Further, the components 402, 404, 406 can be monolithic. Alternatively, the components 402, 404, 406 can be made from different biocompatible materials. For example, the inferior component 402 and the superior component 404 can be made from a first biocompatible material and the central component 406 can be made from a second biocompatible material. Also, the first biocompatible material can have a Young's modulus that is substantially greater than a Young's modulus of the second biocompatible material. Accordingly, as described in greater detail below, an elasticity of the central component 406 can allow the inferior component 402 to be bent, or folded, relative to the superior component 404.

In a particular embodiment, the components 402, 404, 406 can be made from the same biocompatible material. However, in a certain embodiment, the inferior component 402 and the superior component 404 can be cross-linked, but not the central component 406. As such, the Young's modulus of the inferior component 402 and the superior component 404 can be greater than the central component 404.

As illustrated in FIG. 4 and FIG. 5, the inferior component 402 can include an inferior support post 410. An inferior lateral arm 412 can extend from the inferior support post 410. Further, an inferior spinous process bracket 414 can extend from the inferior lateral arm 412.

In a particular embodiment, a lateral cross-section of the inferior support post 410 can indicate that the inferior support post 410 can be generally box-shaped. Alternatively, the inferior support post 410 can be generally cylindrical, generally prismatic, generally polyhedral, or a combination thereof.

As indicated in FIG. 4 and FIG. 5, the inferior spinous process bracket 414 can be generally U shaped. Alternatively, the inferior spinous process bracket 414 can be generally V shaped. Further, the inferior spinous process bracket 414 can include an inferior spinous process engagement structure 422 that extends from the inferior spinous process bracket 414. In a particular embodiment, the inferior spinous process engagement structure 422 can be one or more spikes, one or more teeth, a combination thereof, or some other structure configured to engage a spinous process.

The inferior component 402 can also include a first inferior tether hole 430 and a second inferior tether hole 432. An inferior tether 434 can span the inferior component 402, e.g., between the first inferior tether hole 430 and the second inferior tether hole 432. Further, the inferior tether 434 can be looped at least partially around a spinous process and can substantially maintain the spinous process in contact with the inferior spinous process bracket 414. The tether can comprise a biocompatible elastomeric material that flexes during installation and provides a resistance fit against the inferior process. Further, the tether can comprise a substantially non-resorbable suture or the like.

As illustrated in FIG. 4 and FIG. 5, the superior component 404 can include a superior support post 450. A superior lateral arm 452 can extend from the superior support post 450. Further, a superior spinous process bracket 454 can extend from the superior lateral arm 452.

In a particular embodiment, the superior support post 450 can be sized and shaped similar to the inferior support post 410. A lateral cross-section of the superior support post 450 can indicate that the superior support post 450 can be generally box-shaped. Alternatively, the superior support post 450 can be generally cylindrical, generally prismatic, generally polyhedral, or a combination thereof.

As indicated in FIG. 4 and FIG. 5, the superior spinous process bracket 454 can be generally U shaped. Alternatively, the superior spinous process bracket 454 can be generally V shaped. Further, the superior spinous process bracket 454 can include a superior spinous process engagement structure 460 that extends from the superior spinous process bracket 454. In a particular embodiment, the superior spinous process engagement structure 460 can be one or more spikes, one or more teeth, a combination thereof, or some other structure configured to engage a spinous process.

The superior component 404 can also include a first superior tether hole 470 and a second superior tether hole 472. A superior tether 474 can span the superior component 404, e.g., between the first superior tether hole 470 and the second superior tether hole 472. Further, the superior tether 474 can be looped at least partially around a spinous process and can substantially maintain the spinous process in contact with the superior spinous process bracket 454. The tether can comprise a biocompatible elastomeric material that flexes during installation and provides a resistance fit against the inferior process. Further, the tether can comprise a substantially non-resorbable suture or the like.

FIG. 4 through FIG. 8 further indicate that the interspinous process brace 400 can include a locking sleeve 480 that can be slidably disposed around the inferior component 402, the superior component 404, the central component 406, or a combination thereof. The locking sleeve 480 can include a pair of inferior locking holes 482 and a pair of superior locking holes 416. Also, the inferior component 402 can include a locking hole 486 and the superior component 404 can include a locking hole 488.

In a particular embodiment, the locking sleeve 480 can be moved along the interspinous process brace 400 until the inferior locking holes 482 on the locking sleeve 480 are aligned with the locking hole 486 in the inferior component 402 and the superior locking holes 416 on the locking sleeve 480 are aligned with the locking hole 488 in the superior component 404. Thereafter, as shown in FIG. 5, an inferior locking pin 490 can be installed through the inferior locking holes 482 on the locking sleeve 480 and the locking hole 486 in the inferior component 402. Also, a superior locking pin 492 can be installed through the superior locking holes 416 on the locking sleeve 480 and the locking hole 488 in the superior component 404.

Figure 6:
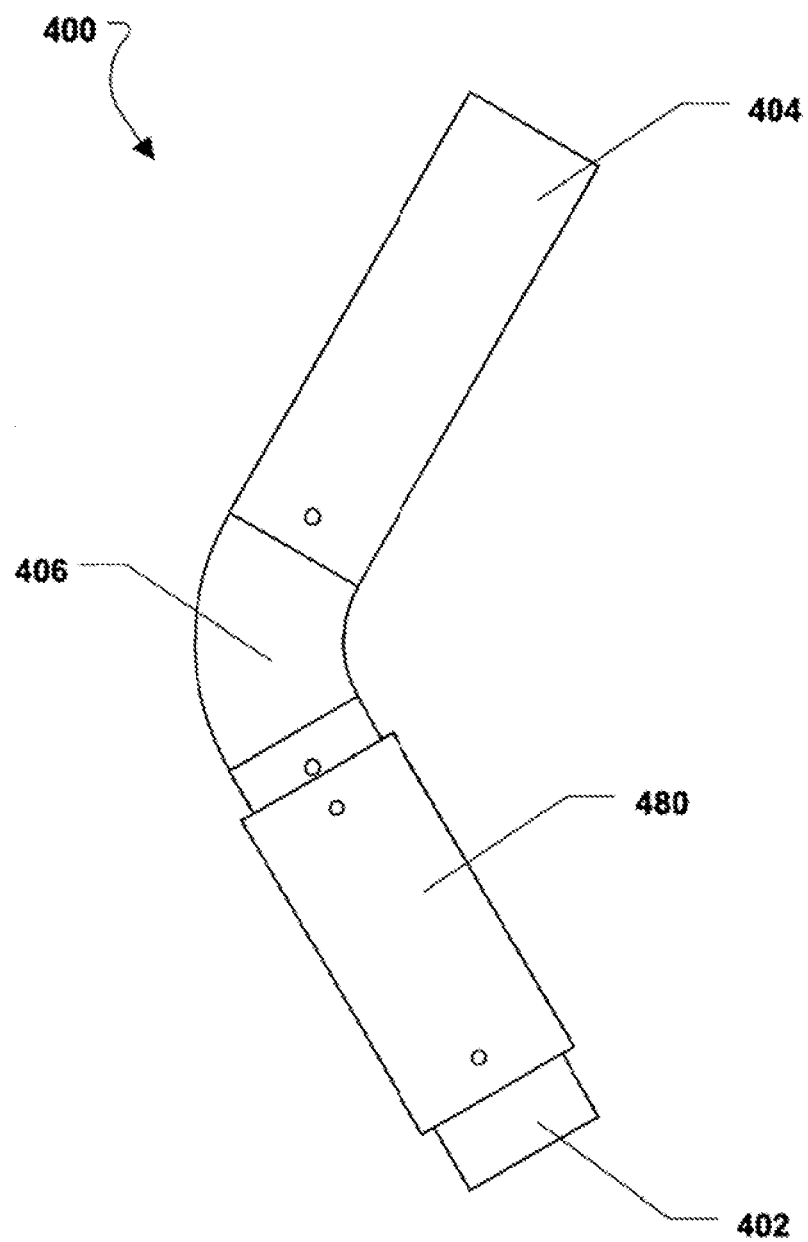
FIG. 6 is a side plan view of the first interspinous process spacer in a bent configuration.
Figure 7:
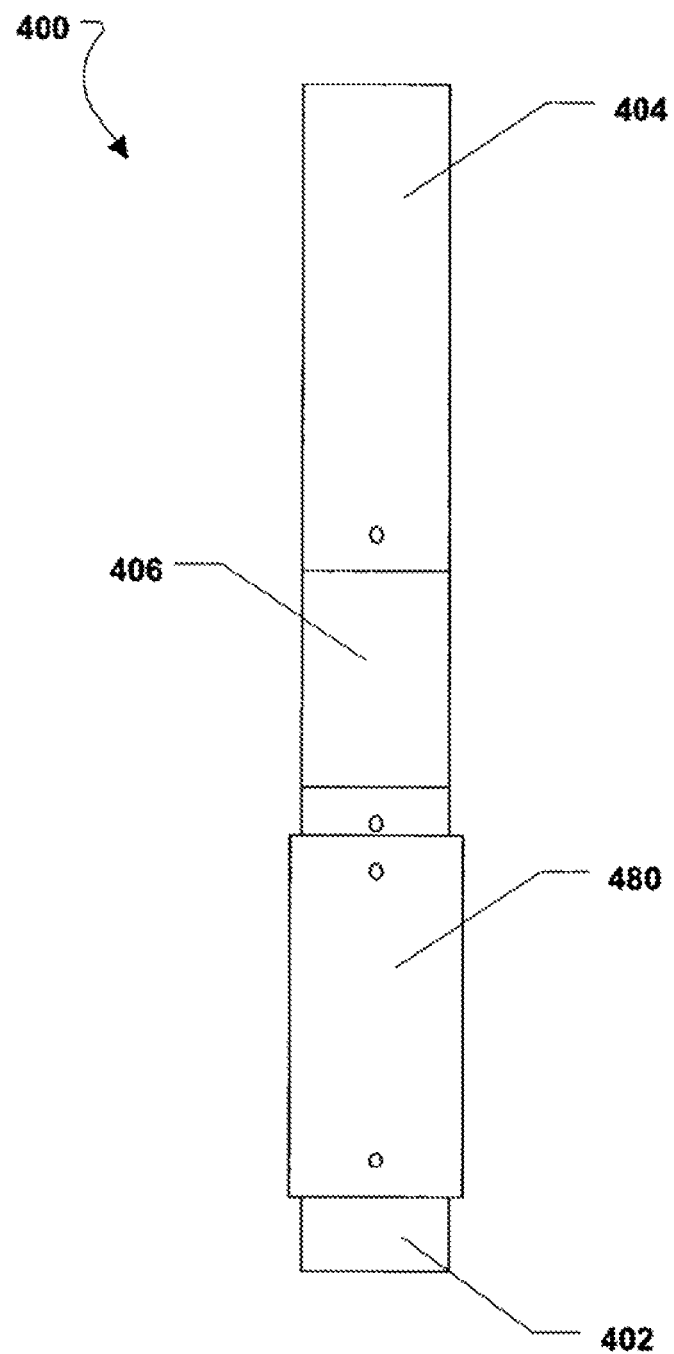
FIG. 7 is a side plan view of the first interspinous process spacer in a straight configuration with a locking sleeve unlocked.
Figure 8:
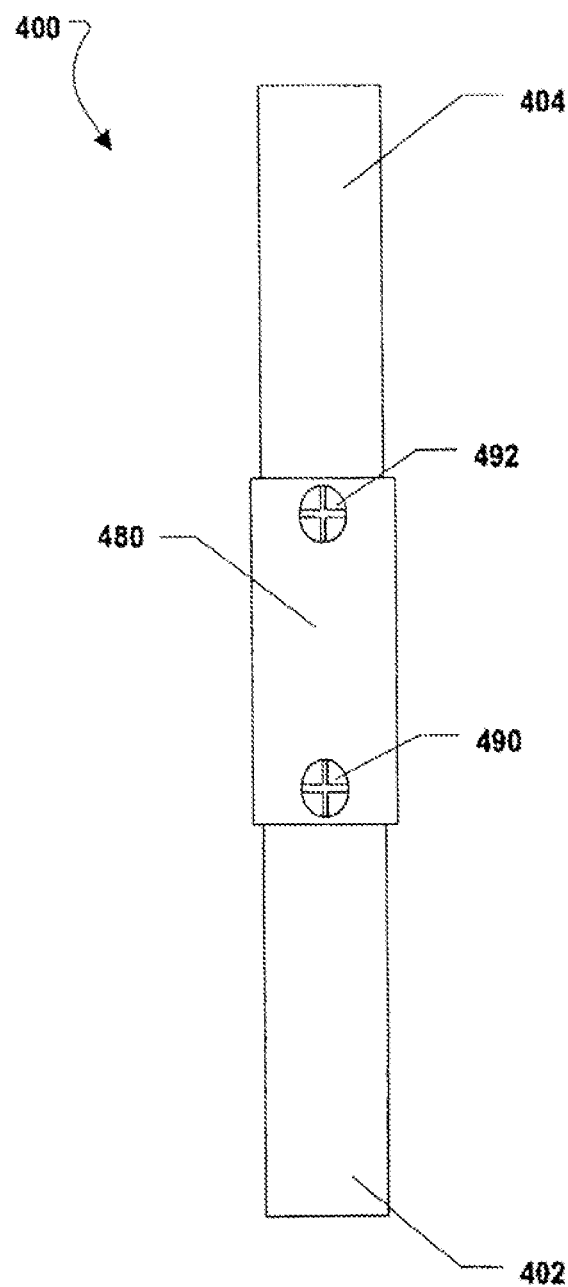
FIG. 8 is a side plan view of the first interspinous process spacer in a straight configuration with the locking sleeve locked.

FIG. 6 illustrates the locking sleeve 480 in an unlocked position and the interspinous process brace 400 in a bent configuration. FIG. 7 illustrates the locking sleeve 480 in an unlocked position and the interspinous process brace 400 in a straight configuration. Further, FIG. 8 illustrates the interspinous process brace 400 in the straight configuration and the locking sleeve 480 in a locked position. Accordingly, the interspinous process brace 400 can be moved between the straight configuration and the bent configuration to facilitate installation between adjacent spinous processes.

More particularly, the interspinous process brace 400 can be bent, or otherwise folded, as shown in FIG. 6, in order to reduce an overall height of the interspinous process brace 400. Thereafter, the interspinous process brace 400 can be place between adjacent spinous processes and allowed to return to the straight configuration, shown in FIG. 7. Further, after the interspinous process brace 400 is allowed to return to the straight configuration, the locking sleeve 480 can be moved to the locked position, shown in FIG. 8, to prevent the interspinous process brace 400 from returning to the bent configuration.

In a particular embodiment, when the interspinous process brace 400 is properly installed between a superior vertebra and an inferior vertebra, shown in FIG. 4, the inferior spinous process bracket 414 can engage and support an inferior spinous process 500. Further, the superior spinous process bracket 454 can engage and support a superior spinous process 502. More specifically, the inferior spinous process engagement structure 422 can extend slightly into and engage the inferior spinous process 500. Also, the superior spinous process engagement structure 460 can extend slightly into and engage the superior spinous process 502. Accordingly, the spinous process engagement structures 422, 460 and the tethers 434, 474 can substantially prevent the interspinous process brace 400 from migrating with respect to the spinous processes 500, 502.

Also, in a particular embodiment, a distractor can be used to increase a distance 510 between the superior spinous process 502 and the inferior spinous process 500 and the interspinous process brace 400 can be installed to support the superior spinous process 502 and the inferior spinous process 500. After the interspinous process brace 400 is installed, the distractor can be removed and the interspinous process brace 400 can support the superior spinous process 502 and the inferior spinous process 500 to substantially prevent the distance 510 between the superior spinous process 502 and the inferior spinous process 500 from returning to a pre-distraction value. Further, the interspinous process brace 400, when locked, as described herein, the interspinous process brace 400 can dynamically resist compressive loads, tensile loads, or a combination thereof. It may be desirable to allow the interspinous process brace 400 to bend or flex after it is installed. Therefore, the locking sleeve 480 may be omitted from the interspinous process brace 400.

Description of a Second Embodiment of an Interspinous Process Brace

Figure 9:
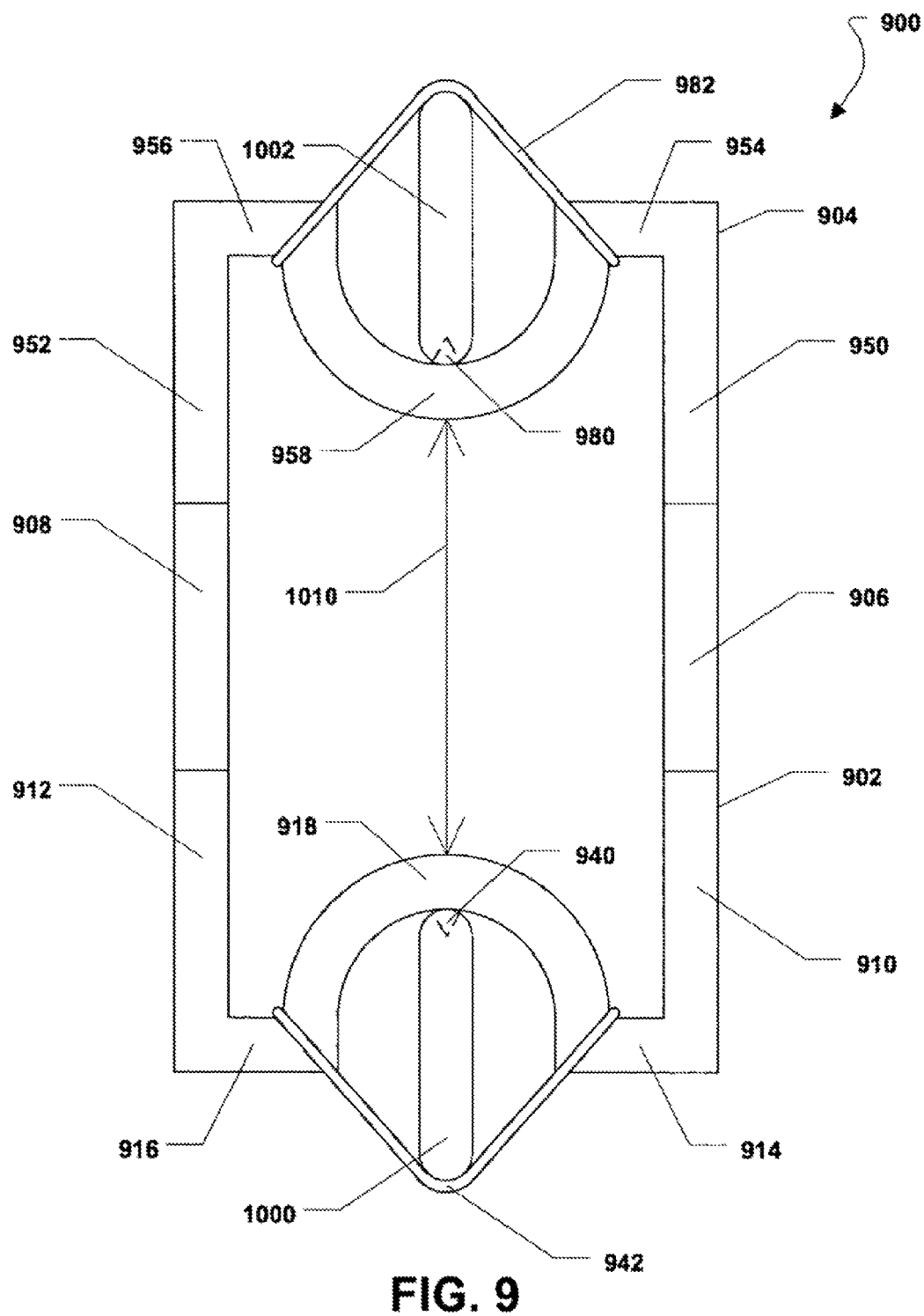
FIG. 9 is a rear plan view of a second interspinous process spacer.
Figure 10:
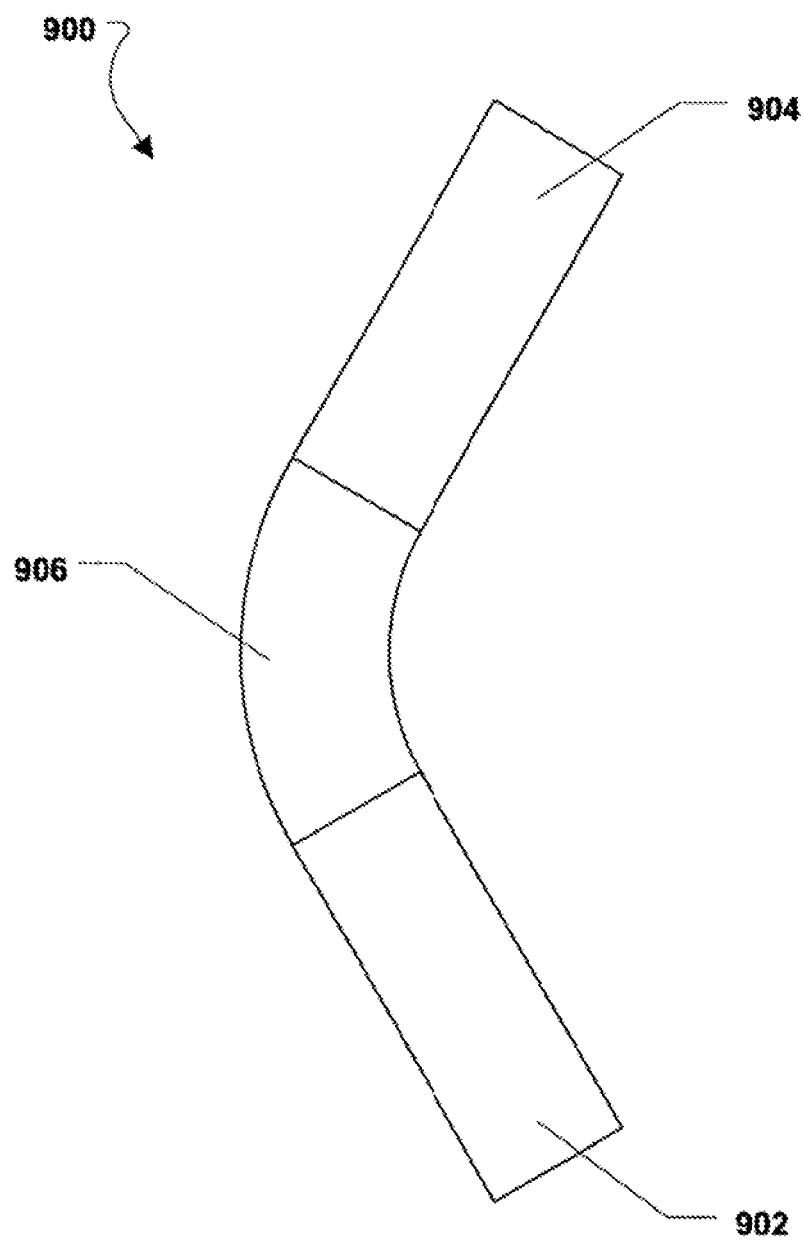
FIG. 10 is a side plan view of the second interspinous process spacer in a bent configuration.
Figure 11:
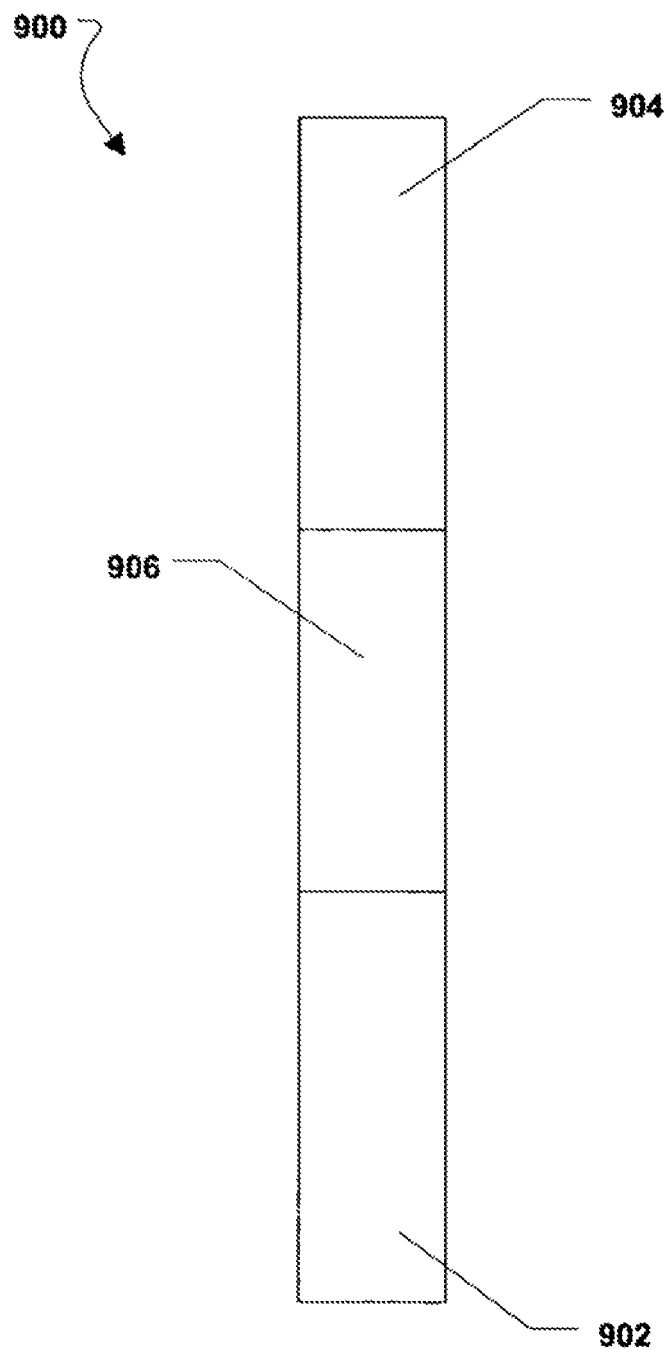
FIG. 11 is a side plan view of the second interspinous process spacer in a straight configuration.

Referring to FIG. 9 through FIG. 11, a second interspinous process brace is shown and is generally designated 900. As shown, the interspinous process brace 900 includes an inferior component 902 and a superior component 904. Further, the inferior component 902 can be coupled, or otherwise connected, to the superior component 904 via a first central component 906 and a second central component 908. In a particular embodiment, the components 902, 904, 906, 908 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the components 902, 904 can be made from any other substantially rigid biocompatible materials.

In a particular embodiment, the components 902, 904, 906, 908 can be made from the same biocompatible material. Further, the components 902, 904, 906, 908 can be monolithic. Alternatively, the components 902, 904, 906, 908 can be made from different biocompatible materials. For example, the inferior component 902 and the superior component 904 can be made from a first biocompatible material and the central components 906, 908 can be made from a second biocompatible material. Also, the first biocompatible material can have a Young's modulus that is substantially greater than a Young's modulus of the second biocompatible material. Accordingly, as described in greater detail below, an elasticity of the central components 906, 908 can allow the inferior component 902 to be bent, or folded, relative to the superior component 904.

As illustrated in FIG. 9 and FIG. 10, the inferior component 902 can include a first inferior support post 910 and a second inferior support post 912. A first inferior lateral arm 914 can extend from the first inferior support post 910 and a second inferior lateral arm 916 can extend from the second inferior support post 912. Further, an inferior spinous process bracket 918 can extend between the first inferior lateral arm 914 and the second inferior lateral arm 916.

In a particular embodiment, a lateral cross-section of the inferior support posts 910, 912 can indicate that the inferior support posts 910, 912 can be generally box-shaped. Alternatively, the inferior support posts 910, 912 can be generally cylindrical, generally prismatic, generally polyhedral, or a combination thereof.

As indicated in FIG. 9 and FIG. 10, the inferior spinous process bracket 918 can be generally U shaped. Alternatively, the inferior spinous process bracket 918 can be generally V shaped. Further, the inferior spinous process bracket 918 can include an inferior spinous process engagement structure 940 that extends from the inferior spinous process bracket 918. In a particular embodiment, the inferior spinous process engagement structure 940 can be one or more spikes, one or more teeth, a combination thereof, or some other structure configured to engage a spinous process.

The inferior component 902 can also include an inferior tether 942 that can be wrapped around the inferior component 902, e.g., around the inferior spinous process bracket 918. In particular embodiment, the inferior tether 942 can be looped at least partially around a spinous process and can substantially maintain the spinous process in contact with the inferior spinous process bracket 918. The tether can comprise a biocompatible elastomeric material that flexes during installation and provides a resistance fit against the inferior process. Further, the tether can comprise a substantially non-resorbable suture or the like.

As illustrated in FIG. 9 and FIG. 10, the superior component 904 can include a first superior support post 950 and a second superior support post 952. A first superior lateral arm 954 can extend from the first superior support post 950 and a second superior lateral arm 956 can extend from the second superior support post 952. Further, a superior spinous process bracket 958 can extend between the first superior lateral arm 954 and the second superior lateral arm 956.

In a particular embodiment, the first superior support post 950 can be sized and shaped to match the first inferior support post 910. Also, the second superior support post 952 can be sized and shaped to match the second inferior support post 912. A lateral cross-section of the superior support posts 950, 952 can indicate that the superior support posts 950, 952 can be solid and generally box-shaped. Alternatively, the superior support posts 950, 952 can be generally cylindrical, generally prismatic, generally polyhedral, or a combination thereof.

As indicated in FIG. 9 and FIG. 10, the superior spinous process bracket 958 can be generally U shaped. Alternatively, the superior spinous process bracket 958 can be generally V shaped. Further, the superior spinous process bracket 958 can include a superior spinous process engagement structure 980 that extends from the superior spinous process bracket 958. In a particular embodiment, the superior spinous process engagement structure 980 can be one or more spikes, one or more teeth, a combination thereof, or some other structure configured to engage a spinous process.

The superior component 904 can also include a superior tether 982 that can be wrapped around the superior component 904, e.g., around the superior spinous process bracket 958. In particular embodiment, the superior tether 982 can be looped at least partially around a spinous process and can substantially maintain the spinous process in contact with the superior spinous process bracket 958. The tether can comprise a biocompatible elastomeric material that flexes during installation and provides a resistance fit against the inferior process. Further, the tether can comprise a substantially non-resorbable suture or the like.

FIG. 10 illustrates the interspinous process brace 900 in a bent configuration. FIG. 11 illustrates the interspinous process brace 900 in a straight configuration. Accordingly, the interspinous process brace 900 can be moved between the straight configuration and the bent configuration to facilitate installation between adjacent spinous processes.

More particularly, the interspinous process brace 900 can be bent, or otherwise folded, as shown in FIG. 10, in order to reduce an overall height of the interspinous process brace 900. Thereafter, the interspinous process brace 900 can be place between adjacent spinous processes and allowed to return to the straight configuration, shown in FIG. 11.

In a particular embodiment, when the interspinous process brace 900 is properly installed between a superior vertebra and an inferior vertebra, as shown in FIG. 9, the inferior spinous process bracket 918 can engage and support an inferior spinous process 1000. Further, the superior spinous process bracket 958 can engage and support a superior spinous process 1002. More specifically, the inferior spinous process engagement structure 940 can extend slightly into and engage the inferior spinous process 1000. Also, the superior spinous process engagement structure 980 can extend slightly into and engage the superior spinous process 1002. Accordingly, the spinous process engagement structures 940, 980 and the tethers 942, 982 can substantially prevent the interspinous process brace 900 from migrating with respect to the spinous processes 1000, 1002.

In a particular embodiment, a distractor can be used to increase the distance 1010 between the superior spinous process 1002 and the inferior spinous process 1000 and the interspinous process brace 900 can be installed to support the superior spinous process 1002 and the inferior spinous process 1000. After the interspinous process brace 900 is installed, the distractor can be removed and the interspinous process brace 900 can support the superior spinous process 1002 and the inferior spinous process 1000 to substantially prevent the distance 1010 between the superior spinous process 1002 and the inferior spinous process 1000 from returning to a pre-distraction value.

Further, the interspinous process brace 900 can include one or more locking sleeves (not shown) similar to the locking sleeve described in conjunction with the first interspinous process brace, described above, in order to lock the interspinous process brace 900 and prevent the interspinous process brace 900 from returning to the bent configuration. When locked, the interspinous process brace 900 can dynamically resist compressive loads, tensile loads, or a combination thereof.

Description of a Third Embodiment of an Interspinous Process Brace

Referring to FIG. 12 through FIG. 17, a third interspinous process brace is shown and is generally designated 1200. As shown, the interspinous process brace 1200 can include an inferior spinous process bracket 1202 and a superior spinous process bracket 1204. The inferior spinous process bracket 1202 can be coupled to the inferior spinous process bracket 1204 by a central component 1206. In a particular embodiment, the brackets 1202, 1204 and the central component 1206 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinylacrylate, polyvinylpyrrolidone, or a combination thereof. Alternatively, the brackets 1202, 1204 can be made from any other substantially rigid biocompatible materials.

In a particular embodiment, the brackets 1202, 1204 and the central component 1206 can be made from the same biocompatible material. Further, the brackets 1202, 1204 and the central component 1206 can be monolithic. Alternatively, the brackets 1202, 1204 and the central component 1206 can be made from different biocompatible materials. For example, the inferior spinous process bracket 1202 and the superior spinous process bracket 1204 can be made from a first biocompatible material and the central component 1206 can be made from a second biocompatible material. Also, the first biocompatible material can have a Young's modulus that is substantially greater than a Young's modulus of the second biocompatible material. Accordingly, as described in greater detail below, an elasticity of the central component 1206 can allow the inferior spinous process bracket 1202 to be bent, or folded, relative to the superior spinous process bracket 1204.

Figure 12:
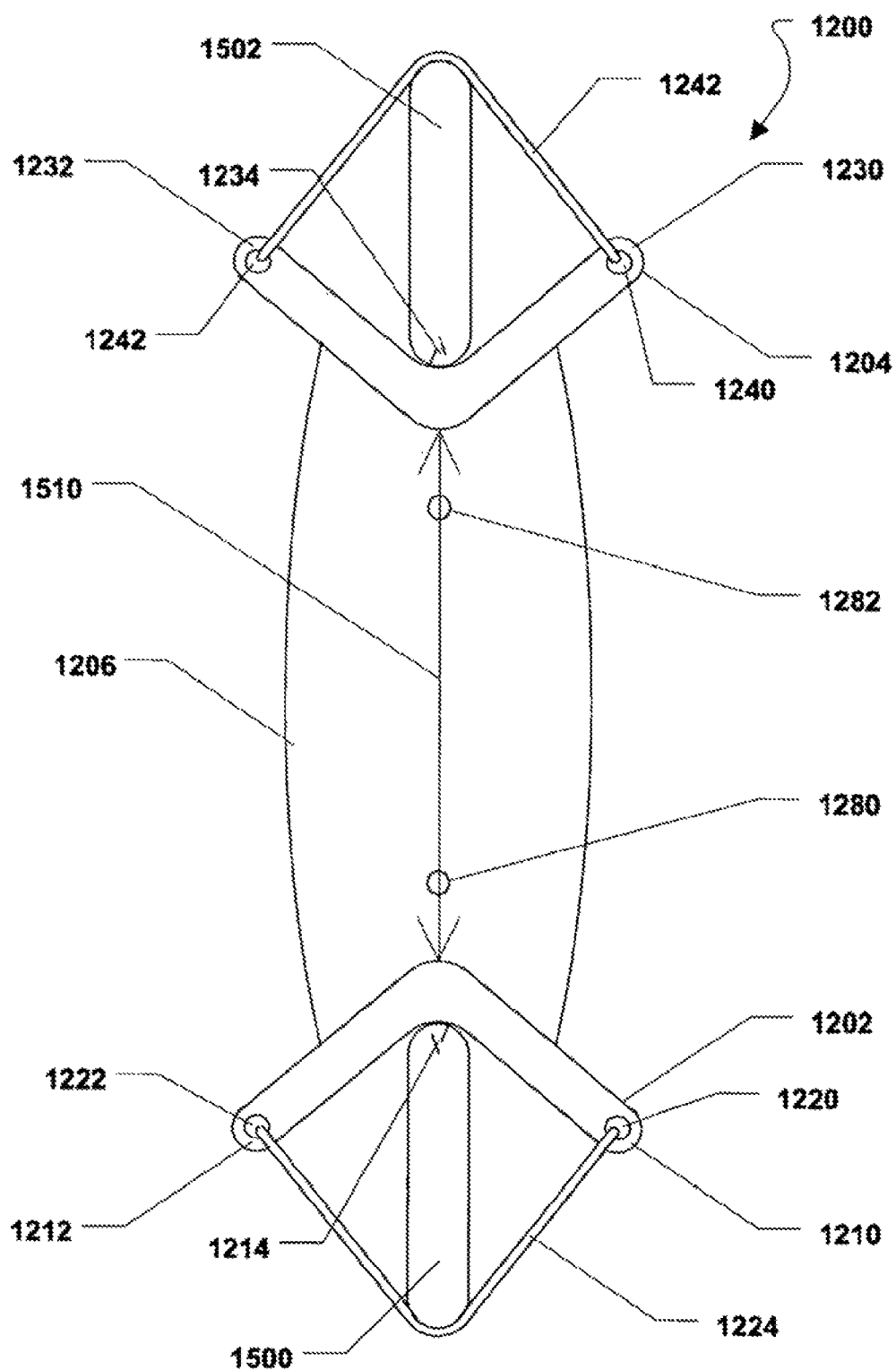
FIG. 12 is a rear plan view of a third interspinous process spacer.
Figure 13:
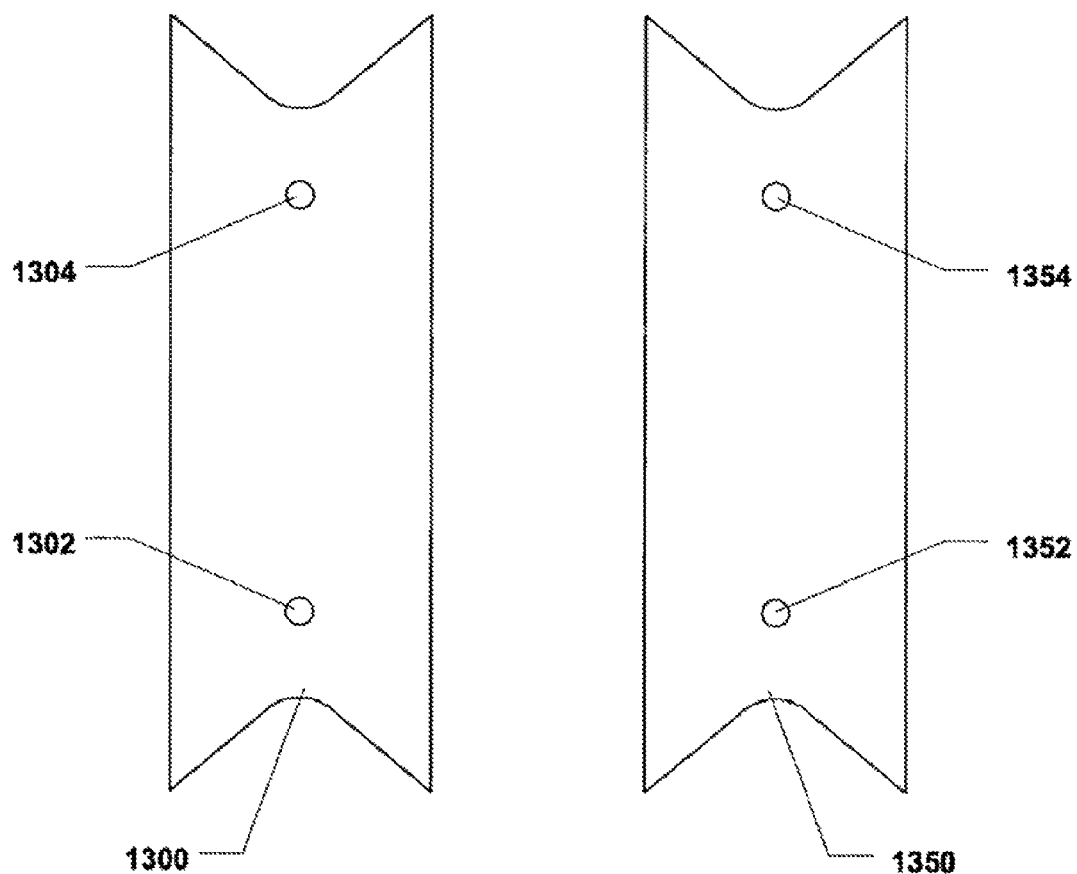
FIG. 13 is a plan view of a posterior locking plate configured to engage the third interspinous process spacer.

As indicated in FIG. 12 and FIG. 13, the inferior spinous process bracket 1202 can be generally V shaped and can include a first inferior support arm 1210 and a second inferior support arm 1212. Alternatively, the inferior spinous process bracket 1202 can be generally U shaped. Further, the inferior spinous process bracket 1202 can include an inferior spinous process engagement structure 1214 that extends from the inferior spinous process bracket 1202. In a particular embodiment, the inferior spinous process engagement structure 1214 can be one or more spikes, one or more teeth, a combination thereof, or some other structure configured to engage a spinous process.

The inferior spinous process bracket 1202 can also include a first inferior tether hole 1220 and a second inferior tether hole 1222. An inferior tether 1224 can span the inferior spinous process bracket 1202, e.g., between the first inferior tether hole 1220 and the second inferior tether hole 1222. Further, the inferior tether 1224 can be looped at least partially around a spinous process and can substantially maintain the spinous process in contact with the inferior spinous process bracket 1202. The tether can comprise a biocompatible elastomeric material that flexes during installation and provides a resistance fit against the inferior process. Further, the tether can comprise a substantially non-resorbable suture or the like.

Further, the superior spinous process bracket 1204 can be generally V shaped and can include a first superior support arm 1230 and a second superior support arm 1232. Alternatively, the superior spinous process bracket 1204 can be generally U shaped. The superior spinous process bracket 1204 can also include a superior spinous process engagement structure 1234 that extends from the superior spinous process bracket 1204. In a particular embodiment, the superior spinous process engagement structure 1234 can be one or more spikes, one or more teeth, a combination thereof, or some other structure configured to engage a spinous process.

The superior spinous process bracket 1204 can also include a first superior tether hole 1240 and a second superior tether hole 1242. A superior tether 1244 can span the superior spinous process bracket 1204, e.g., between the first superior tether hole 1240 and the second superior tether hole 1242. Further, the superior tether 1244 can be looped at least partially around a spinous process and can substantially maintain the spinous process in contact with the superior spinous process bracket 1204. The tether can comprise a biocompatible elastomeric material that flexes during installation and provides a resistance fit against the inferior process. Further, the tether can comprise a substantially non-resorbable suture or the like.

As illustrated in FIG. 12, the central component 1206 can be formed with an inferior locking hole 1280 and a superior locking hole 1282. The locking holes 1280, 1282 can be configured to receive respective locking pins, described below.

Figure 14:
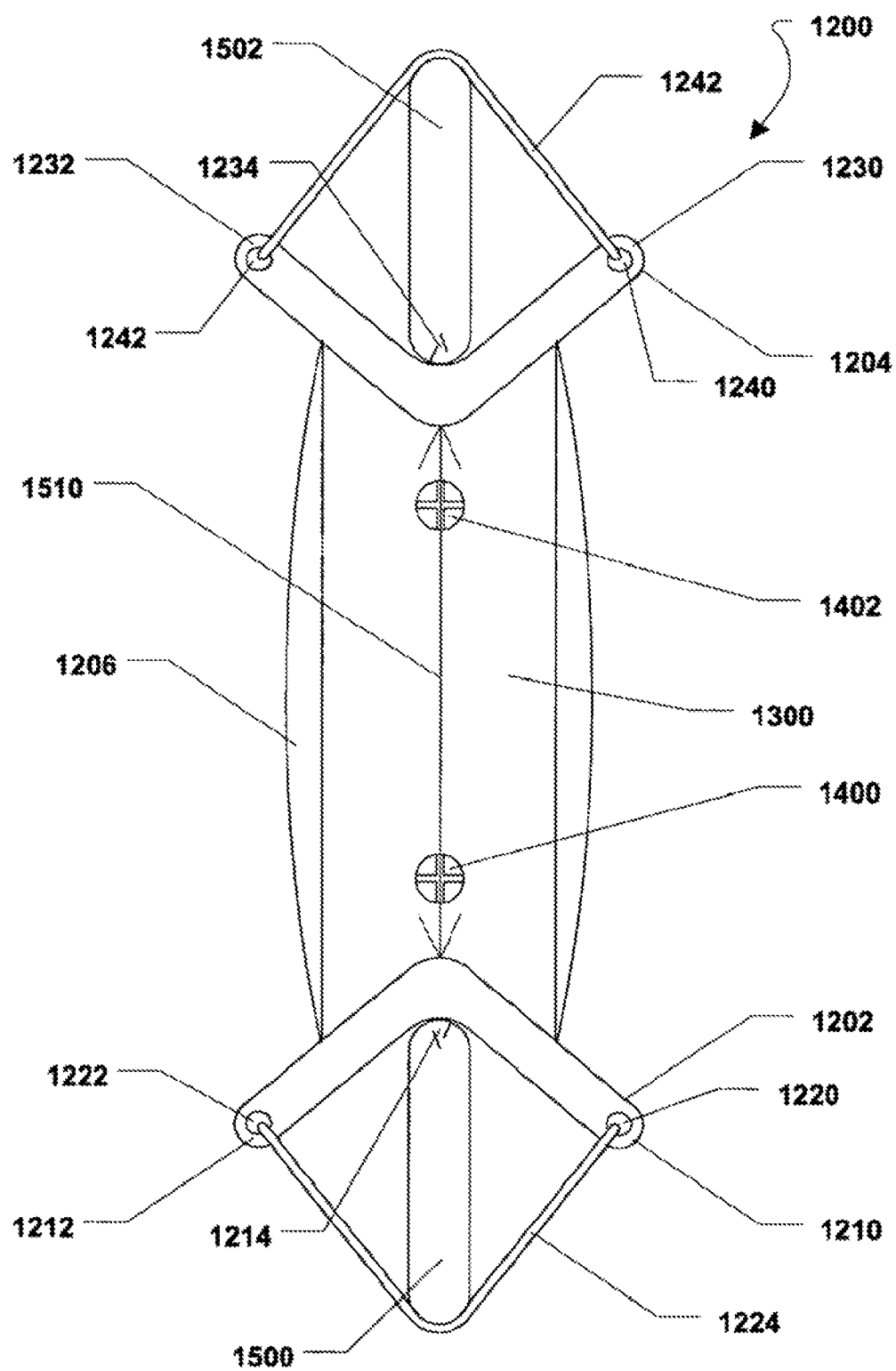
FIG. 14 is a rear plan view of the third interspinous process spacer with the posterior locking plate engaged therewith.
Figure 16:
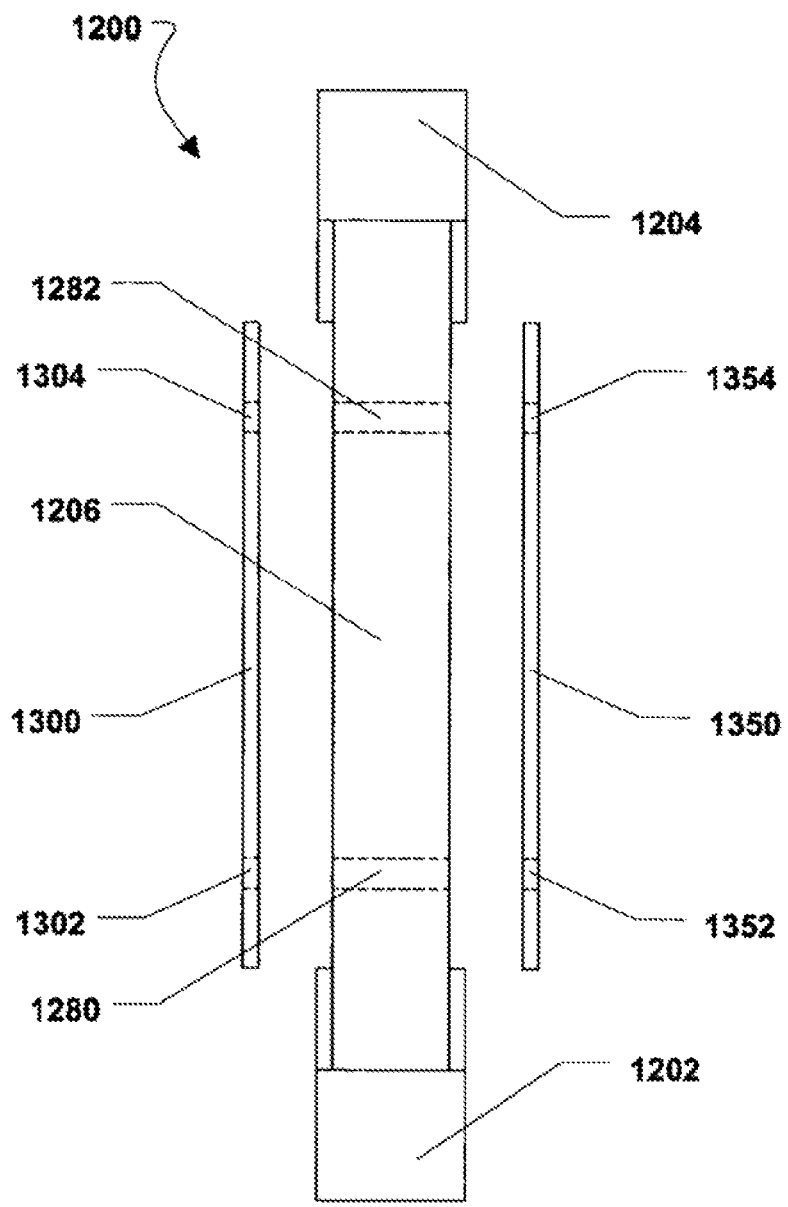
Figure 17:
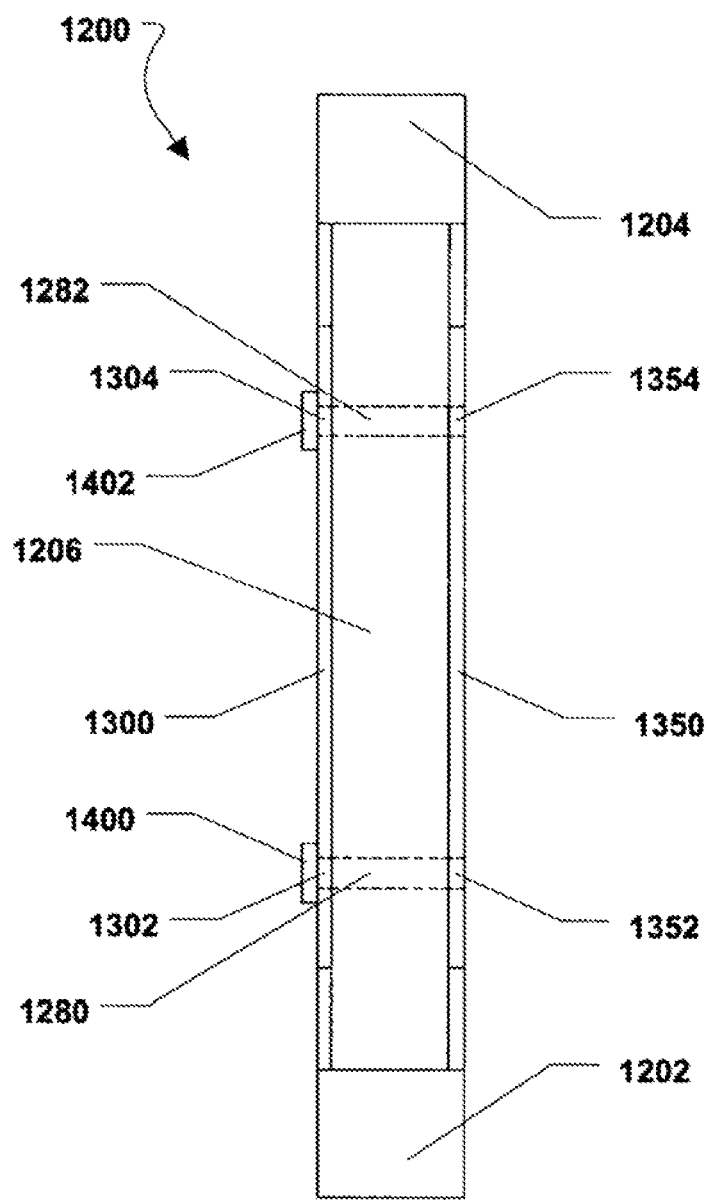
FIG. 17 is a side plan view of the third interspinous process spacer in the straight configuration with the posterior locking plate and the anterior locking plate engaged therewith.

FIG. 13 illustrates a posterior locking plate 1300 that can include an inferior locking hole 1302 and a superior locking hole 1304. Also, FIG. 13 illustrates an anterior locking plate 1350 that can include an inferior locking hole 1352 and a superior locking hole 1354. In a particular embodiment, as shown in FIG. 16 and FIG. 17, the locking plates 1300, 1350 can be placed around the central component 1206 between the brackets 1202, 1204 such that the central component 806 is sandwiched between the locking plates 1300, 1350. FIG. 14 illustrates the posterior locking plate 1300 installed between the inferior spinous process bracket 1202 and the superior spinous process bracket 1204.

Further, as shown in FIG. 14 and FIG. 17, an inferior locking pin 1400 can be installed through the inferior locking hole 1302 in the posterior locking plate 1300 and the inferior locking hole 1280 in the central component 806. In a particular embodiment, the inferior locking pin 1400 can threadably engage the inferior locking hole 1352 formed in the anterior locking plate 1350. Also, a superior locking pin 1402 can be installed through the superior locking hole 1304 in the posterior locking plate 1300 and the superior locking hole 1282 in the central component 1206. The superior locking pin 1402 can threadably engage the superior locking hole 1354 formed in the anterior locking plate 1350.

Figure 15:
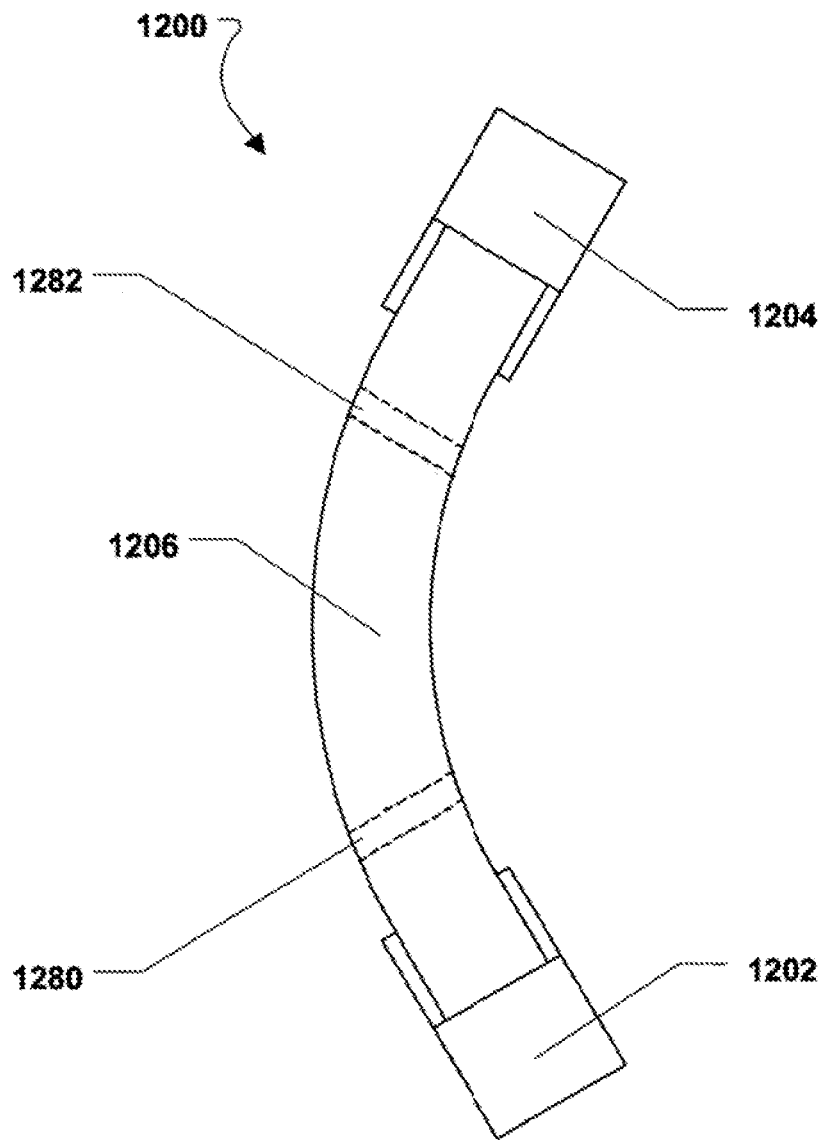
FIG. 15 is a side plan view of the third interspinous process spacer in a bent configuration.

FIG. 15 illustrates the interspinous process brace 1200 in a bent configuration with the locking plates 1300, 1350 disengaged therefrom. FIG. 16 illustrates the interspinous process brace 1200 in a straight configuration with the locking plates 1300, 1350 disengaged therefrom. Further, FIG. 17 illustrates the interspinous process brace 1200 in the straight configuration and the locking plates 1300, 1350 engaged therewith. Accordingly, the interspinous process brace 1200 can be moved between the straight configuration and the bent configuration to facilitate installation between adjacent spinous processes.

More particularly, the interspinous process brace 1200 can be bent, or otherwise folded, as shown in FIG. 15, in order to reduce an overall height of the interspinous process brace 1200. Thereafter, the interspinous process brace 1200 can be place between an inferior spinous process 1500 and a superior spinous process 1502 and allowed to return to the straight configuration, shown in FIG. 14 and FIG. 16. Further, after the interspinous process brace 1200 is allowed to return to the straight configuration, the locking plates 1300, 1350 can be installed, as described herein, to prevent the interspinous process brace 1200 from returning to the bent configuration.

In a particular embodiment, a distractor can be used to increase a distance 1510 between the superior spinous process 1502 and the inferior spinous process 1500 and the interspinous process brace 1200 can be installed to support the superior spinous process 1502 and the inferior spinous process 1500. After the interspinous process brace 1200 is installed, the distractor can be removed and the interspinous process brace 1200 can support the superior spinous process 1502 and the inferior spinous process 1500 to substantially prevent the distance 1510 between the superior spinous process 1502 and the inferior spinous process 1500 from returning to a pre-distraction value. Further, the interspinous process brace 1200, when locked, can dynamically resist compressive loads, tensile loads, or a combination thereof.

Description of a Fourth Embodiment of an Interspinous Process Brace

Figure 18:
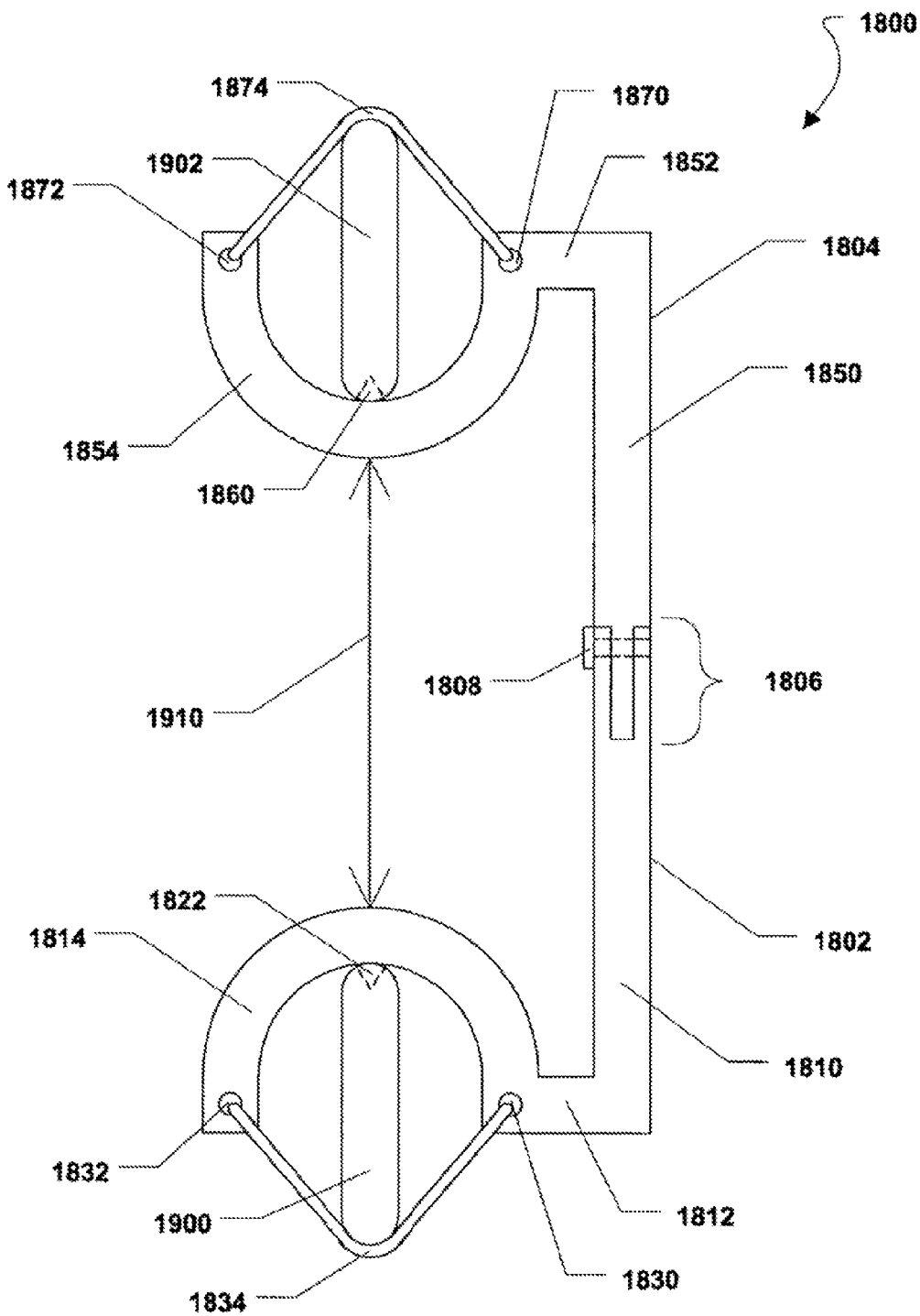
FIG. 18 is a rear plan view of a fourth interspinous process spacer.
Figure 19:
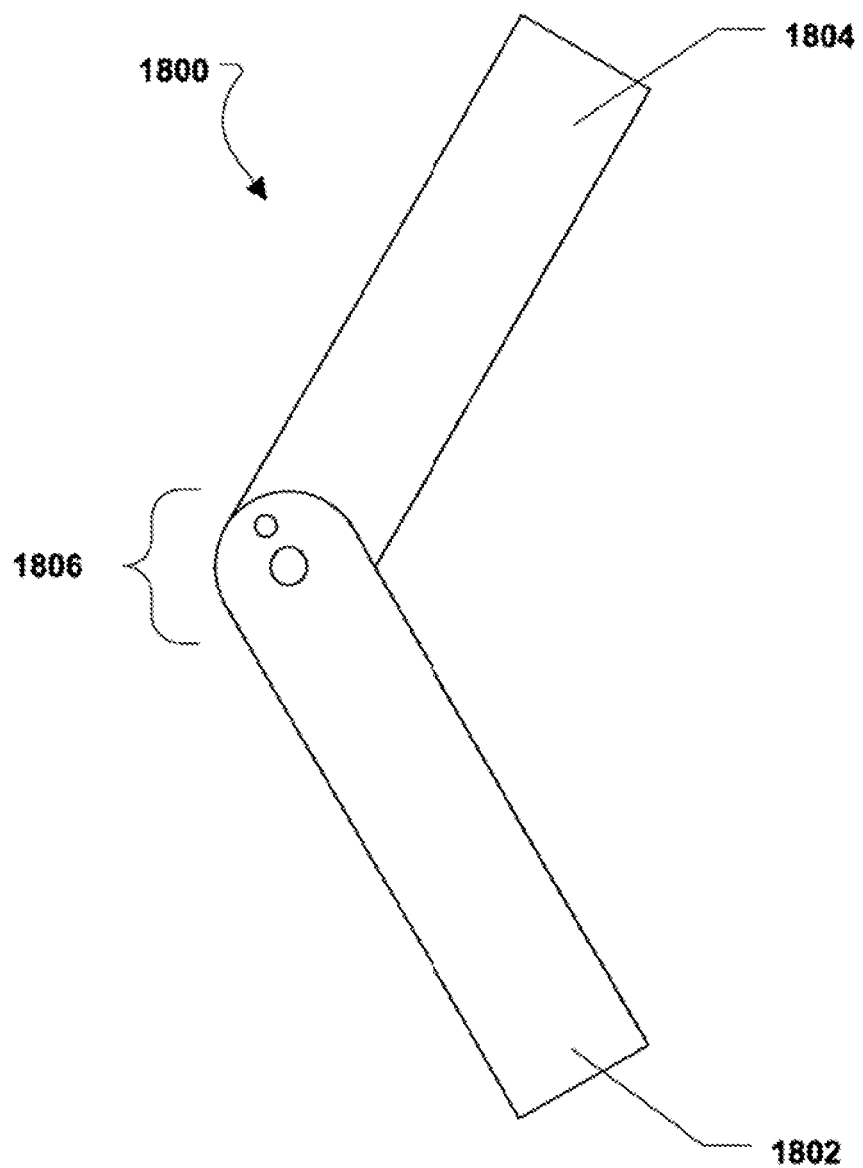
FIG. 19 is a side plan view of the fourth interspinous process spacer in a bent configuration.
Figure 20:
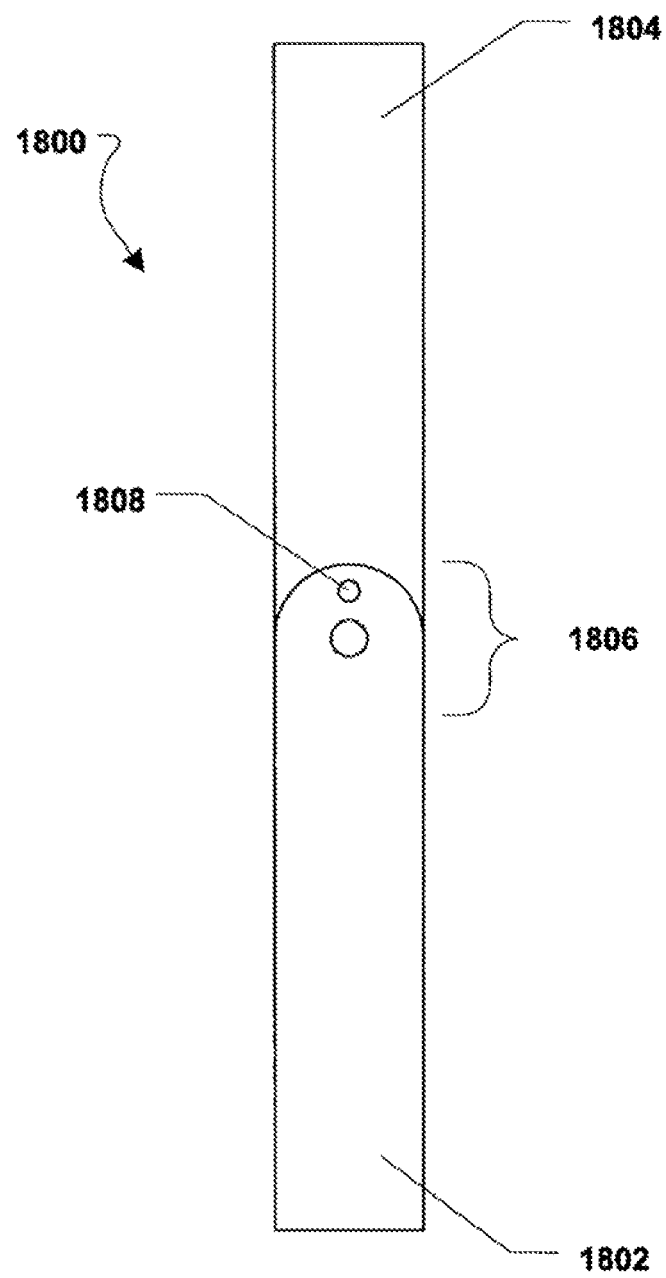
FIG. 20 is a side plan view of the fourth interspinous process spacer in a straight configuration.

Referring to FIG. 18 through FIG. 20, a first interspinous process brace is shown and is generally designated 1800. As shown in FIG. 18, the interspinous process brace 1800 can include an inferior component 1802 and a superior component 1804. Further, the inferior component 1802 can be coupled, or otherwise connected, to the superior component 1804 via a central hinge 1806. A locking pin 1808 can be disposed within the central hinge 1806 in order to lock the central hinge 1806. In an alternative embodiment, in lieu of a hinge, a ball-and-socket joint (not shown) can couple the inferior component 1802 and the superior component 1804. Further, a locking sleeve, similar to the locking sleeve described above, can be used to lock the central hinge 1806 instead of the locking pin 1808.

In a particular embodiment, the components 1802, 1804 can be made from one or more biocompatible materials. For example, the materials can be metal containing materials, polymer materials, or composite materials that include metals, polymers, or combinations of metals and polymers.

In a particular embodiment, the metal containing materials can be metals. Further, the metal containing materials can be ceramics. Also, the metals can be pure metals or metal alloys. The pure metals can include titanium. Moreover, the metal alloys can include stainless steel, a cobalt-chrome-molybdenum alloy, e.g., ASTM F-999 or ASTM F-75, a titanium alloy, or a combination thereof.

The polymer materials can include polyurethane materials, polyolefin materials, polyaryletherketone (PAEK) materials, silicone materials, hydrogel materials, or a combination thereof. Further, the polyolefin materials can include polypropylene, polyethylene, halogenated polyolefin, flouropolyolefin, or a combination thereof. The polyaryletherketon (PAEK) materials can include polyetherketone (PEK), polyetheretherketone (PEEK), polyetherketoneketone (PEKK), polyetherketoneetherketoneketone (PEKEKK), or a combination thereof. The hydrogels can include polyacrylamide, poly-N-isopropylacrylamine, polyvinyl methylether, polyvinyl alcohol, polyethyl hydroxyethyl cellulose, poly (2-ethyl) oxazoline, polyethyleneoxide, polyethylglycol, polyethylene glycol, polyacrylic acid, polyacrylonitrile, polyvinyl acrylate, polyvinylpyrrolidone, or a combination thereof. Alternatively, the components 1802, 1804 can be made from any other substantially rigid biocompatible materials.

As illustrated in FIG. 18 and FIG. 19, the inferior component 1802 can include an inferior support post 1810. An inferior lateral arm 1812 can extend from the inferior support post 1810. Further, an inferior spinous process bracket 1814 can extend from the inferior lateral arm 1812.

In a particular embodiment, a lateral cross-section of the inferior support post 1810 can indicate that the inferior support post 1810 can be generally box-shaped. Alternatively, the inferior support post 1810 can be generally cylindrical, generally prismatic, generally polyhedral, or a combination thereof.

As indicated in FIG. 18 and FIG. 19, the inferior spinous process bracket 1814 can be generally U shaped. Alternatively, the inferior spinous process bracket 1814 can be generally V shaped. Further, the inferior spinous process bracket 1814 can include an inferior spinous process engagement structure 1822 that extends from the inferior spinous process bracket 1814. In a particular embodiment, the inferior spinous process engagement structure 1822 can be one or more spikes, one or more teeth, a combination thereof, or some other structure configured to engage a spinous process.

The inferior component 1802 can also include a first inferior tether hole 1830 and a second inferior tether hole 1832. An inferior tether 1834 can span the inferior component 1802, e.g., between the first inferior tether hole 1830 and the second inferior tether hole 1832. Further, the inferior tether 1834 can be looped at least partially around a spinous process and can substantially maintain the spinous process in contact with the inferior spinous process bracket 1814. The tether can comprise a biocompatible elastomeric material that flexes during installation and provides a resistance fit against the inferior process. Further, the tether can comprise a substantially non-resorbable suture or the like.

As illustrated in FIG. 18 and FIG. 19, the superior component 1804 can include a superior support post 1850. A superior lateral arm 1852 can extend from the superior support post 1850. Further, a superior spinous process bracket 1854 can extend from the superior lateral arm 1852.

In a particular embodiment, the superior support post 1850 can be sized and shaped similar to the inferior support post 1810. A lateral cross-section of the superior support post 1850 can indicate that the superior support post 1850 can be generally box-shaped. Alternatively, the superior support post 1850 can be generally cylindrical, generally prismatic, generally polyhedral, or a combination thereof.

As indicated in FIG. 18 and FIG. 19, the superior spinous process bracket 1854 can be generally U shaped. Alternatively, the superior spinous process bracket 1854 can be generally V shaped. Further, the superior spinous process bracket 1854 can include a superior spinous process engagement structure 1862 that extends from the superior spinous process bracket 1854. In a particular embodiment, the superior spinous process engagement structure 1862 can be one or more spikes, one or more teeth, a combination thereof, or some other structure configured to engage a spinous process.

The superior component 1804 can also include a first superior tether hole 1870 and a second superior tether hole 1872. A superior tether 1874 can span the superior component 1804, e.g., between the first superior tether hole 1870 and the second superior tether hole 1872. Further, the superior tether 1874 can be looped at least partially around a spinous process and can substantially maintain the spinous process in contact with the superior spinous process bracket 1854. The tether can comprise a biocompatible elastomeric material that flexes during installation and provides a resistance fit against the inferior process. Further, the tether can comprise a substantially non-resorbable suture or the like.

FIG. 19 illustrates the interspinous process brace 1800 in a bent configuration. FIG. 20 illustrates the interspinous process brace 1800 in a straight configuration. Accordingly, the interspinous process brace 1800 can be moved between the straight configuration and the bent configuration to facilitate installation between adjacent spinous processes.

More particularly, the locking pin 1808 can be removed and the interspinous process brace 1800 can be bent, or otherwise folded, as shown in FIG. 19, in order to reduce an overall height of the interspinous process brace 1800. Thereafter, the interspinous process brace 1800 can be place between adjacent spinous processes and returned to the straight configuration, shown in FIG. 19. Further, after the interspinous process brace 1800 is returned to the straight configuration, the locking pin 1808 can be installed within the central hinge 1806, to prevent the interspinous process brace 1800 from returning to the bent configuration.

In a particular embodiment, when the interspinous process brace 1800 is properly installed between a superior vertebra and an inferior vertebra, shown in FIG. 18, the inferior spinous process bracket 1814 can engage and support an inferior spinous process 1900. Further, the superior spinous process bracket 1854 can engage and support a superior spinous process 1902. More specifically, the inferior spinous process engagement structure 1822 can extend slightly into and engage the inferior spinous process 1900. Also, the superior spinous process engagement structure 1862 can extend slightly into and engage the superior spinous process 1902. Accordingly, the spinous process engagement structures 1822, 1862 and the tethers 1834, 1874 can substantially prevent the interspinous process brace 1800 from migrating with respect to the spinous processes 1900, 1902.

Also, in a particular embodiment, a distractor can be used to increase a distance 1910 between the superior spinous process 1902 and the inferior spinous process 1900 and the interspinous process brace 1800 can be installed to support the superior spinous process 1902 and the inferior spinous process 1900. After the interspinous process brace 1800 is installed, the distractor can be removed and the interspinous process brace 1800 can support the superior spinous process 1902 and the inferior spinous process 1900 to substantially prevent the distance 1910 between the superior spinous process 1902 and the inferior spinous process 1900 from returning to a pre-distraction value.

Description of a Method of Treating a Spine

Figure 21:
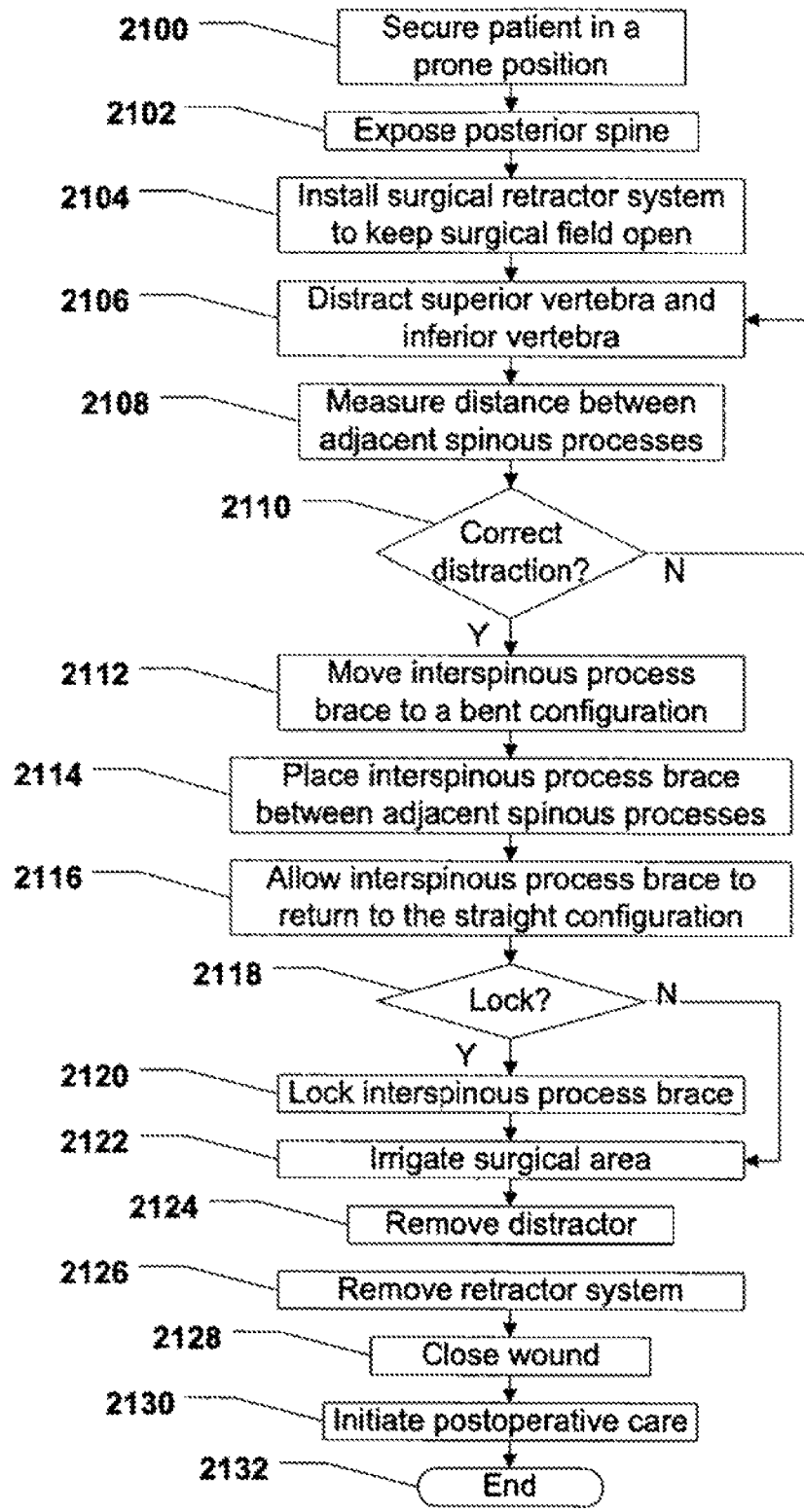
FIG. 21 is a flow chart illustrating a method of treating a spine.

Referring to FIG. 21, a method of treating a spine is shown and commences at block 2100. At block 2100, a patient can be secured on an operating table. Depending on the surgical approach to be used, the patient can be secured in a prone position for a posterior approach, a supine position for an anterior approach, a lateral decubitus position for a lateral approach, or another position well known in the art. At block 2102, the spine can be exposed in order to expose adjacent spinous processes. Further, at block 2104, a surgical retractor system can be installed to keep a surgical field open.

Moving to block 2106, a superior vertebra and inferior vertebra can be distracted. In a particular embodiment, the superior vertebra and inferior vertebra can be distracted using a distractor. At block 2108, a distance between the adjacent spinous processes can be measured. Thereafter, at block 2110 it is determined whether the distraction is correct, e.g., has the superior vertebra and inferior vertebral been distracted such that a distance between the adjacent spinous processes has reached a value that a surgeon has deemed therapeutic. For example, the superior vertebra and inferior vertebra can be distracted in order to reduce or obviate impingement on a nerve root.

If the distraction is not correct, the method can return to block 2106 and the superior vertebra and inferior vertebra can be further distracted. Conversely, if the distraction is correct, the method can move to block 2112 and an interspinous process brace can be moved to a bent configuration. The interspinous process brace can be an interspinous process brace in accordance with one or more embodiments described herein. At block 2114, the interspinous process brace can be installed between the adjacent spinous processes. Further, at block 2116, the interspinous process brace can be allowed to return to the straight configuration.

Moving to decision step 2118, it can be determined whether to lock the interspinous process brace. In a particular embodiment, this determination can be based on any degradation of the particular vertebral joint that is being repair, any degradation of the surrounding facet joints, any degradation of the adjacent processes, or a combination thereof. If it is determined to lock the interspinous process brace, the method can move to block 2120 and the interspinous process brace can be locked. For example, one or more locking sleeves on the interspinous process brace can be moved to a locked position to prevent the interspinous process brace from bending. Alternatively, one or more locking plates can be installed in the interspinous process brace to prevent the interspinous process brace from bending. From block 2120, the method proceeds to block 2122.

It is noted that multiple braces can be supplied in kit form for field use with each brace corresponding to a different distraction distance, such that the proper post distraction positioning of the processes can be maintained. Alternatively or in addition, the kit can contain locking pins and/or discrete, separable locking plates if the brace configuration receives such plates.

Returning to decision step 2118, if it is determined not to lock the interspinous process brace, the method can move directly to block 2122 and the surgical area can be irrigated. At block 2124, a distractor can be removed. Also, at block 2126, the retractor system can be removed. Further, at block 2128, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 2130, postoperative care can be initiated. The method can end at state 2132.

In another embodiment, an interspinous process brace according to one or more of the embodiments described herein can be used to distract a superior spinous process and an inferior spinous process. For example, the interspinous process brace can be bent and placed between a superior spinous process and inferior spinous process. Thereafter, the interspinous process brace can be straightened. As the interspinous process brace is straightened, it can distract the superior spinous process and the inferior spinous process. After the spinous processes are distracted, the interspinous process brace can remain in place.

Alternatively, the interspinous process brace can be used to distract the spinous processes and an implant can be installed between a superior vertebra and an inferior vertebra. After the implant is installed between the superior vertebra and the inferior vertebra, the interspinous process brace can be returned to the bent configuration and removed. In a particular embodiment, the implant can be a one-piece intervertebral prosthetic disc, a two-piece intervertebral prosthetic disc, a three-piece intervertebral prosthetic disc, a solid nucleus implant, an inflatable nucleus implant, an expandable nucleus implant, a fusion cage, or some other similar device.

CONCLUSION

With the configuration of structure described above, the interspinous process brace provides a device that can be used to treat a spine and substantially alleviate or minimize one or more symptoms associated with disc degeneration, facet joint degeneration, or a combination thereof. For example, the interspinous process brace can installed between adjacent spinous processes in order to support the spinous processes and maintain them at or near a predetermined distance there between.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An interspinous process brace, comprising:
    a superior spinous process bracket configured to engage a superior spinous process;
    an inferior spinous process bracket configured to engage an inferior spinous process, the superior and inferior spinous process brackets defining a first axis;
    a central component connecting the superior spinous process bracket and the inferior spinous process bracket, the central component defining a second axis offset from the first axis such that, when implanted in a patient, the central component is disposed along a side of an adjacent spinous processes, wherein the central component is configured to allow the interspinous process brace to move between a bent configuration and a straight configuration, wherein in the bent configuration an overall height of the interspinous process brace is minimized to facilitate installation between the superior spinous process and the inferior spinous process;
    further comprising a posterior locking plate, wherein the posterior locking plate is configured to prevent the interspinous process brace from moving to the bent configuration when affixed to the central component.

2. The interspinous process brace of claim 1 wherein the posterior locking plate is configured to be installed between the superior spinous process bracket and the inferior spinous process bracket adjacent to the central component.

3. The interspinous process brace of claim 2 further comprising an anterior locking plate, wherein the anterior locking plate is configured to prevent the interspinous process brace from moving to the bent configuration when affixed to the central component.

4. The interspinous process brace of claim 3 wherein the anterior locking plate is configured to be installed between the superior spinous process bracket and the inferior spinous process bracket adjacent to the central component.

5. The interspinous process brace of claim 1: wherein the posterior plate comprises first and second holes therethrough; further comprising first and second locking pins extending through the first and second holes, respectively, so as to secure the posterior locking plate to the central component.

6. The interspinous process brace of claim 1 wherein the superior spinous process bracket is generally V-shaped.

7. The interspinous process brace of claim 6 wherein the inferior spinous process bracket is generally V-shaped.

8. The interspinous process brace of claim 1 wherein the superior spinous process bracket is generally U-shaped.

9. The interspinous process brace of claim 8 wherein the inferior spinous process bracket is generally U-shaped.

10. The interspinous process brace of claim 1 wherein the superior spinous process bracket, the inferior spinous process bracket, and the central component are monolithically formed.

11. The interspinous process brace of claim 1 further comprising a tether having respective ends secured to the superior spinous process bracket.

12. The interspinous process brace of claim 11 wherein the superior spinous process bracket comprises at least a first tether hole; wherein the tether extends through the first tether hole.

13. The interspinous process brace of claim 11 wherein the tether is elastomeric.

14. An interspinous process brace, comprising:
a superior spinous process bracket including a superior tether configured to loop partially around and engage a superior spinous process;
an inferior spinous process bracket including a superior tether configured to loop partially around and engage an inferior spinous process, the superior and inferior spinous process brackets defining a first axis;
a central component connecting the superior spinous process bracket and the inferior spinous process bracket, the central component defining a second axis offset from the first axis, wherein the central component is configured to allow the interspinous process brace to move between a bent configuration and a straight configuration, wherein in the bent configuration an overall height of the interspinous process brace is minimized to facilitate installation between the superior spinous process and the inferior spinous process;
further comprising a posterior locking plate, wherein the posterior locking plate is configured to prevent the interspinous process brace from moving to the bent configuration when affixed to the central component.

* * * * *